United States Patent
Dalal et al.

(10) Patent No.: US 10,952,910 B2
(45) Date of Patent: Mar. 23, 2021

(54) ELASTOMERIC LAMINATE WITH SOFT NONCRIMPED SPUNBOND FIBER WEBS

(71) Applicant: The Procter & Gamble Company, Cincinnati, OH (US)

(72) Inventors: Urmish Popatlal Dalal, Milford, OH (US); Todd Douglas Lenser, Liberty Township, OH (US); LeAnn Nichole Phillips, Cincinnati, OH (US); Christine A. Methena, Cincinnati, OH (US); Miguel Angel Caballero, Cincinnati, OH (US); Tanner Laurie Williams, Loveland, OH (US)

(73) Assignee: The Procter & Gamble Company, Cincinnati, OH (US)

(*) Notice: Subject to any disclaimer, the term of this patent is extended or adjusted under 35 U.S.C. 154(b) by 198 days.

(21) Appl. No.: 15/937,235

(22) Filed: Mar. 27, 2018

(65) Prior Publication Data

US 2018/0271716 A1    Sep. 27, 2018

Related U.S. Application Data

(60) Provisional application No. 62/476,892, filed on Mar. 27, 2017.

(51) Int. Cl.
*A61F 13/49* (2006.01)
*A61F 13/514* (2006.01)
(Continued)

(52) U.S. Cl.
CPC .. *A61F 13/49012* (2013.01); *A61F 13/15203* (2013.01); *A61F 13/49009* (2013.01);
(Continued)

(58) Field of Classification Search
CPC ........ A61F 13/494011; A61F 13/49012; A61F 13/49014; A61F 13/49015;
(Continued)

(56) References Cited

U.S. PATENT DOCUMENTS 3,113,225 A    12/1963    Kleesattel et al.
3,338,992 A    8/1967    Allison
(Continued)

FOREIGN PATENT DOCUMENTS

CN    103434239 B    11/2015
CN    104837455 B    4/2018
(Continued)

OTHER PUBLICATIONS

International Search Report, PCT/US2019/024011, dated Jul. 4, 2019, 14 pages.
(Continued)

*Primary Examiner* — Catharine L Anderson
(74) *Attorney, Agent, or Firm* — Wednesday G. Shipp

(57) ABSTRACT

An absorbent article includes a first waist region, a second waist region, and a crotch region disposed between the first and second waist regions. The article also includes a chassis having a topsheet, a backsheet, and an absorbent core disposed between the topsheet and backsheet; and an ear joined to the chassis. The ear includes a laminate formed from a first nonwoven and second nonwoven and an elastomeric material sandwiched between said first and second nonwovens. The laminate further includes a plurality of ultrasonic bonds; and the first nonwoven includes an exterior surface having an average TS750 value of 5 db V2rms or less.

18 Claims, 10 Drawing Sheets

(51) Int. Cl.
*A61F 13/15* (2006.01)
*A61L 15/22* (2006.01)
*A61L 15/24* (2006.01)
*A61L 15/60* (2006.01)
*D04H 3/007* (2012.01)
*D04H 3/018* (2012.01)
*D04H 3/16* (2006.01)
*A61F 13/513* (2006.01)

(52) U.S. Cl.
CPC .. *A61F 13/49011* (2013.01); *A61F 13/49014* (2013.01); *A61F 13/49015* (2013.01); *A61F 13/514* (2013.01); *A61L 15/225* (2013.01); *A61L 15/24* (2013.01); *A61L 15/60* (2013.01); *D04H 3/007* (2013.01); *D04H 3/018* (2013.01); *D04H 3/16* (2013.01); *A61F 2013/15284* (2013.01); *A61F 2013/15292* (2013.01); *A61F 2013/15406* (2013.01); *A61F 2013/15552* (2013.01); *A61F 2013/15869* (2013.01); *A61F 2013/4903* (2013.01); *A61F 2013/49022* (2013.01); *A61F 2013/49034* (2013.01); *A61F 2013/49084* (2013.01); *A61F 2013/49093* (2013.01); *A61F 2013/51338* (2013.01); *D10B 2321/022* (2013.01); *D10B 2509/026* (2013.01)

(58) Field of Classification Search
CPC .. A61F 2013/15284; A61F 2013/15357; A61F 2013/49023; A61F 2013/49025; A61F 2013/51078; A61F 2013/5108; A61F 2013/51083; A61F 2013/51085; A61F 2013/51088; A61F 2013/51338
See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long et al. |
| 3,802,817 A | 4/1974 | Matsuki et al. |
| 3,848,594 A | 11/1974 | Buell |
| 3,849,241 A | 11/1974 | Butin et al. |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,573,986 A | 3/1986 | Minetola et al. |
| 4,610,678 A | 9/1986 | Weisman et al. |
| 4,629,643 A | 12/1986 | Curro |
| 4,634,440 A | 1/1987 | Widlund |
| 4,662,875 A | 5/1987 | Hirotsu et al. |
| 4,673,402 A | 6/1987 | Weisman et al. |
| 4,780,352 A | 10/1988 | Palumbo |
| 4,785,996 A | 11/1988 | Ziecker et al. |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,854,984 A | 8/1989 | Ball |
| 4,888,231 A | 12/1989 | Angstadt |
| 4,892,536 A | 1/1990 | Desmarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen et al. |
| 5,151,092 A | 2/1992 | Buell et al. |
| 5,092,861 A | 3/1992 | Nomura |
| 5,137,537 A | 8/1992 | Herron et al. |
| 5,143,679 A | 9/1992 | Weber |
| 5,147,345 A | 9/1992 | Young et al. |
| 5,149,720 A | 9/1992 | Desmarais |
| 5,156,793 A | 10/1992 | Buell et al. |
| 5,167,897 A | 12/1992 | Weber et al. |
| 5,221,274 A | 6/1993 | Buell et al. |
| 5,242,436 A | 9/1993 | Weil |
| 5,246,433 A | 9/1993 | Hasse |
| 5,260,345 A | 11/1993 | Desmarais et al. |
| 5,266,392 A | 11/1993 | Land |
| 5,269,775 A | 12/1993 | Freeland et al. |
| 5,342,338 A | 8/1994 | Roe |
| 5,360,420 A | 11/1994 | Cook et al. |
| 5,382,400 A | 1/1995 | Pike |
| 5,387,207 A | 2/1995 | Dyer et al. |
| 5,397,316 A | 3/1995 | LaVon et al. |
| 5,418,045 A | 5/1995 | Pike |
| 5,422,172 A | 6/1995 | Wu |
| 5,433,715 A | 7/1995 | Tanzer et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes et al. |
| 5,628,097 A | 5/1997 | Benson |
| 5,635,191 A | 6/1997 | Roe et al. |
| 5,643,588 A | 7/1997 | Roe et al. |
| 5,658,639 A | 8/1997 | Curro et al. |
| 5,665,300 A | 9/1997 | Brignola |
| 5,700,254 A | 12/1997 | McDowall et al. |
| 5,702,551 A | 12/1997 | Huber et al. |
| 5,707,468 A | 1/1998 | Arnold |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline |
| 5,916,661 A | 6/1999 | Benson et al. |
| 5,957,908 A | 9/1999 | Kline |
| 5,968,025 A | 10/1999 | Roe |
| 5,972,806 A | 10/1999 | Weinberger |
| 5,993,432 A | 11/1999 | Lodge et al. |
| 6,004,306 A | 12/1999 | Robles et al. |
| 6,030,373 A | 2/2000 | Vangompel |
| 6,036,796 A | 3/2000 | Halbert |
| 6,096,668 A | 8/2000 | Abuto |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,255,236 B1 | 7/2001 | Cree |
| 6,369,121 B1 | 4/2002 | Catalfamo |
| 6,410,129 B2 | 6/2002 | Zhang et al. |
| 6,426,444 B2 | 7/2002 | Roe et al. |
| 6,432,098 B1 | 8/2002 | Kline et al. |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley et al. |

(56) References Cited

U.S. PATENT DOCUMENTS

| | | |
|---|---|---|
| 6,540,854 B2 | 4/2003 | Couillard |
| 6,555,643 B1 | 4/2003 | Rieger |
| 6,559,262 B1 | 5/2003 | Waymouth |
| 6,572,595 B1 | 6/2003 | Klemp et al. |
| 6,572,598 B1 | 6/2003 | Ashton |
| 6,586,652 B1 | 7/2003 | Roe et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass |
| 6,645,569 B2 | 11/2003 | Cramer et al. |
| 6,649,001 B2 | 11/2003 | Heden |
| 6,677,258 B2 | 1/2004 | Carroll et al. |
| 6,692,477 B2 | 2/2004 | Gibbs |
| 6,713,159 B1 | 3/2004 | Blenke et al. |
| 6,758,925 B1 | 7/2004 | Stegelmann |
| 6,767,420 B2 | 7/2004 | Stegelmann |
| 6,825,393 B2 | 11/2004 | Roe et al. |
| 6,830,800 B2 | 12/2004 | Curro |
| 6,843,134 B2 | 1/2005 | Anderson et al. |
| 6,861,571 B1 | 3/2005 | Roe et al. |
| 6,863,933 B2 | 3/2005 | Cramer et al. |
| 6,878,433 B2 | 4/2005 | Curro |
| 6,974,514 B2 | 12/2005 | Hamulski |
| 7,056,404 B2 | 6/2006 | McFall et al. |
| 7,062,983 B2 | 6/2006 | Anderson et al. |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum et al. |
| 7,819,853 B2 | 10/2010 | Desai et al. |
| 7,824,594 B2 | 11/2010 | Qureshi |
| 7,870,651 B2 | 1/2011 | Middlesworth |
| 7,896,641 B2 | 3/2011 | Qureshi |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi |
| 8,092,438 B2 | 1/2012 | Betts |
| 8,118,801 B2 | 2/2012 | Macura |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai et al. |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck et al. |
| 8,940,116 B2 | 1/2015 | Gilgenbach |
| 9,102,132 B2 | 8/2015 | Wennerbck |
| 9,211,221 B2 | 12/2015 | Macura |
| 9,301,889 B2 | 4/2016 | Miyamoto |
| 9,358,161 B2 | 6/2016 | Lawson et al. |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,524,964 B2 | 1/2020 | Sauer |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0233082 A1 | 12/2003 | Kline |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0224132 A1 | 11/2004 | Roe |
| 2005/0008839 A1 | 1/2005 | Cramer et al. |
| 2005/0065487 A1 | 3/2005 | Graef |
| 2005/0107764 A1 | 5/2005 | Matsuda et al. |
| 2005/0154362 A1 | 7/2005 | Warren |
| 2005/0245162 A1 | 11/2005 | Mccormack |
| 2005/0287892 A1 | 12/2005 | Fouse |
| 2006/0062963 A1 | 3/2006 | Middlesworth |
| 2006/0135024 A1 | 6/2006 | Thomas |
| 2006/0148361 A1 | 7/2006 | Mccormack |
| 2006/0149209 A1* | 7/2006 | Malchow ............... A61F 13/49 604/389 |
| 2006/0287637 A1 | 12/2006 | Lam |
| 2007/0105472 A1 | 5/2007 | Marche |
| 2007/0123124 A1 | 5/2007 | Middlesworth |
| 2007/0142798 A1 | 6/2007 | Goodlander |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge |
| 2008/0003910 A1 | 1/2008 | Hughes |
| 2008/0003911 A1 | 1/2008 | Sabbagh |
| 2008/0051748 A1 | 2/2008 | Black |
| 2008/0076315 A1 | 3/2008 | Mccormack |
| 2008/0119102 A1 | 5/2008 | Hughes |
| 2008/0147031 A1 | 6/2008 | Long |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad et al. |
| 2009/0275909 A1 | 11/2009 | Sakaguchi |
| 2009/0292266 A1 | 11/2009 | Bäck |
| 2009/0294044 A1 | 12/2009 | Gill |

(56) References Cited

U.S. PATENT DOCUMENTS

| | | |
|---|---|---|
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0268183 A1 | 10/2010 | Een |
| 2010/0280481 A1 | 11/2010 | Kline |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0045620 A1 | 2/2012 | Oba |
| 2012/0055613 A1 | 3/2012 | Baeck |
| 2012/0055615 A1 | 3/2012 | Baeck |
| 2012/0061015 A1 | 3/2012 | Lavon et al. |
| 2012/0061016 A1 | 3/2012 | Lavon et al. |
| 2012/0095429 A1 | 4/2012 | Kobayashi |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | Lavon |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider |
| 2013/0218116 A1 | 8/2013 | Schneider |
| 2013/0230700 A1 | 9/2013 | Schoenbeck |
| 2013/0236700 A1 | 9/2013 | Yamanaka |
| 2013/0255861 A1 | 10/2013 | Schneider et al. |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0330232 A1 | 11/2014 | Schönbeck |
| 2014/0377506 A1 | 12/2014 | Eckstein et al. |
| 2014/0377513 A1 | 12/2014 | Galie |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer et al. |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle |
| 2016/0013614 A1 | 1/2016 | Moto |
| 2016/0136014 A1 | 5/2016 | Arora |
| 2016/0167334 A1 | 6/2016 | Arora |
| 2016/0206485 A1 | 7/2016 | Seitz |
| 2016/0270972 A1 | 9/2016 | Surushe et al. |
| 2016/0324697 A1 | 11/2016 | Schoenbeck |
| 2017/0027775 A1 | 2/2017 | Barnes |
| 2017/0056256 A1 | 3/2017 | Smith et al. |
| 2017/0079851 A1 | 3/2017 | Greening |
| 2017/0079854 A1 | 3/2017 | Butler |
| 2017/0087029 A1 | 3/2017 | Nelson |
| 2017/0142806 A1 | 5/2017 | Park |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal et al. |
| 2018/0042778 A1 | 2/2018 | Lenser |
| 2018/0042779 A1 | 2/2018 | Lenser |
| 2018/0042780 A1 | 2/2018 | Lenser et al. |
| 2018/0042784 A1 | 2/2018 | Koshijima |
| 2018/0042785 A1 | 2/2018 | Dalal et al. |
| 2018/0042786 A1 | 2/2018 | Mueller |
| 2018/0042787 A1 | 2/2018 | Lenser et al. |
| 2018/0271716 A1 | 9/2018 | Dalal |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2020/0170846 A1 | 6/2020 | Lenser |
| 2020/0179179 A1 | 6/2020 | Lenser |
| 2020/0268563 A1 | 8/2020 | Lenser |

FOREIGN PATENT DOCUMENTS

| | | |
|---|---|---|
| EP | 1256594 A1 | 11/2002 |
| EP | 1447066 A1 | 8/2004 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 2647360 B1 | 6/2018 |
| JP | 2004223238 A | 8/2004 |
| JP | 2007521036 A | 8/2007 |
| JP | 2011139843 A | 7/2011 |
| JP | 4934835 B2 | 5/2012 |
| JP | 5036641 B2 | 9/2012 |
| JP | 2012524645 A | 10/2012 |
| JP | 6240733 B1 | 11/2017 |
| JP | 2017065142 A | 11/2018 |
| WO | 9510996 A1 | 4/1995 |
| WO | 9511652 A1 | 5/1995 |
| WO | 9516746 A1 | 6/1995 |
| WO | 9828123 A1 | 7/1998 |
| WO | 2000045763 A1 | 8/2000 |
| WO | 2000059430 A1 | 10/2000 |
| WO | 0073031 A1 | 12/2000 |
| WO | 02067809 A2 | 9/2002 |

(56) References Cited

FOREIGN PATENT DOCUMENTS

| | | |
|---|---|---|
| WO | 2003007864 A1 | 1/2003 |
| WO | 2004017882 A2 | 3/2004 |
| WO | 2004017885 A1 | 3/2004 |
| WO | 2004060652 A1 | 7/2004 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | 2008156075 A1 | 12/2008 |
| WO | 2009146307 A1 | 12/2009 |
| WO | 2010055699 A1 | 5/2010 |
| WO | 2010118214 A1 | 10/2010 |
| WO | 2010126415 A1 | 11/2010 |
| WO | 2011080643 A2 | 7/2011 |
| WO | 2011125893 A1 | 10/2011 |
| WO | 2012052172 A1 | 4/2012 |
| WO | 2012030571 A3 | 5/2012 |
| WO | 2012112501 A1 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | 2013163141 A1 | 10/2013 |
| WO | 2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | 2016073713 A1 | 5/2016 |
| WO | 2016109514 A1 | 7/2016 |
| WO | WO2018031841 A1 | 2/2018 |
| WO | WO2018183315 A1 | 10/2018 |
| WO | 2016121979 A1 | 1/2019 |
| WO | 2019089689 A2 | 5/2019 |

OTHER PUBLICATIONS

U.S. Appl. No. 16/916,655, filed Jun. 30, 2020, Nelson Edward Greening, II et al.
Case 14424; PCT International Search Report, Appl. No. PCT/US2017/046388, dated Sep. 22, 2017, 15 pages.
Case 14525; PCT International Search Report and Written Opinion, Appl. No. PCT/US2017/046393, dated Sep. 25, 2017, 16 pages.
Case 14562Q; PCT International Search Report. Appl. No. PCT/US2017/046394, dated Sep. 28, 2017, 15 pages.
Case 14911; PCT International Search Report, Appl. No. PCT/US2017/046395, dated Sep. 20, 2017, 15 pages.
All Office Actions, U.S. Appl. No. 15/674,559.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
Case 14445MQ; International Search Report, Appl. No. PCT/US2017/046397, dated Sep. 28, 2017, 13 pages.
Case 14590MQ: All Office Actions, U.S. Appl. No. 15/674,561.
Case 14590MQ; EP Application No. 17754982.1, Third Party Observation, dated Jun. 17, 2020, 9 pages.
Case 14915Q; EP Application No. 17764961.3, Third Party Observation, dated Aug. 24. 2020, 6 pages.
Case 14756M; International Search Report and Written Opinion, Appl. No. PCT/US2018/024549, dated May 30, 2018, 13 pages.
Case 14590MQ; International Search Report, Appl. No. PCT/US2017/046398, dated Sep. 28, 2017, 13 pages.
Case 14915Q; International Search Report, Appl. No. PCT/US2017/049026, dated Oct. 19, 2017, 13 pages.
Extended European Search Report and Search Opinion; Application No. 20183749.9; dated Nov. 9, 2020; 8 pages.
International Search Report and Written Opinion; Application No. PCT/US2020/070219; dated Oct. 1, 2020; 14 pages.
Unpublished U.S. Appl. No. 17/108,241, filed Dec. 1, 2020, to Urmish Popatlal Dalal et al.

\* cited by examiner

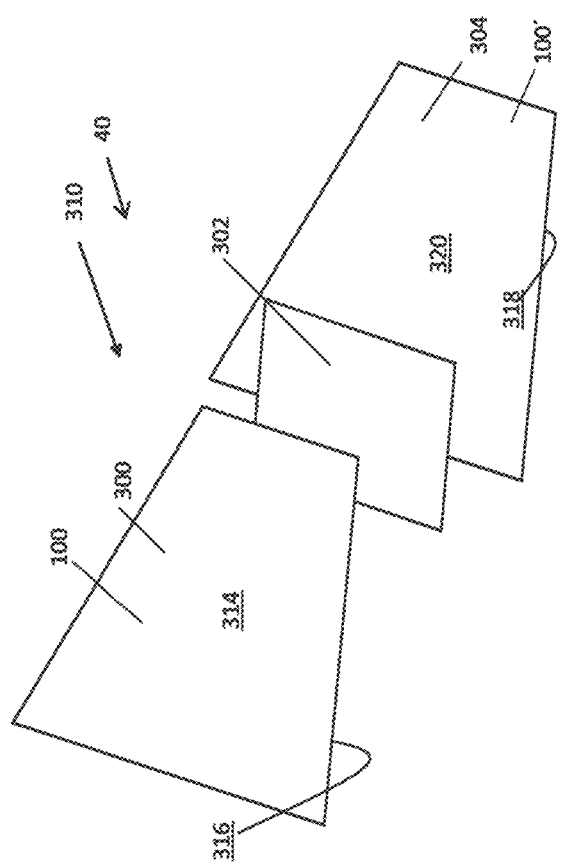

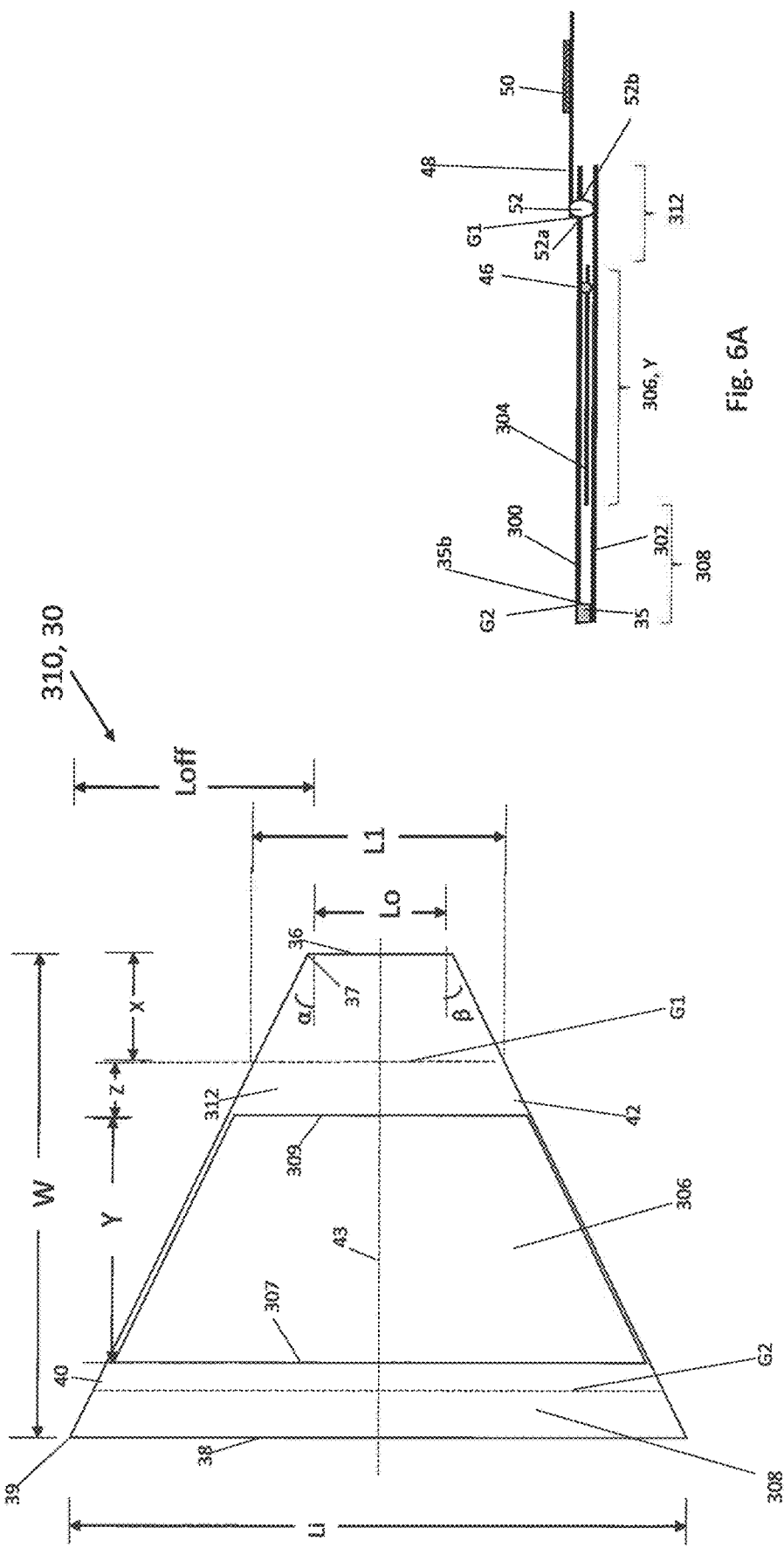

ELASTOMERIC LAMINATE WITH SOFT NONCRIMPED SPUNBOND FIBER WEBS

FIELD OF THE INVENTION

The disclosure herein relates to spunbond fiber nonwoven webs and articles incorporating them, in particular absorbent articles which incorporate said spunbond fiber webs.

BACKGROUND OF THE INVENTION

Elastomeric laminates are used in various products including absorbent articles (e.g., diapers, incontinence articles, feminine hygiene pads). Such laminates typically include an elastomeric layer that provides extensibility to the laminate and an outer layer that is less stretchable but suitable for providing durability and desirable tactile properties. In this way, the laminate permits a component of an article to closely and comfortably contact the wearer while providing desirable exterior qualities.

Elastomeric laminates can be produced by multiple methods. For example, the laminate may be in the form a gathered laminate, wherein the coverstock layer forms rugosities when the elastic layer is relaxed. Said gathered laminates may be formed by extending the elastic layer material to a greater extent than the outer material at the time of lamination. Alternatively, the outer layer material may be corrugated and the elastic material may be in its relaxed state at the time of lamination. In either scenario, following lamination, the coverstock gathers or bunches and forms rugosities when the laminate is in a relaxed state.

Another type of elastomeric laminate is a zero strain laminate. During lamination, the outer and elastic layers are joined at approximately zero relative strain (i.e., both layers are relaxed at approximately zero strain). Zero strain laminates are activated by a mechanical straining process, which creates separations or deformations in the outer layer materials and renders the laminate elastic.

Nonwoven webs are typically used as the outer layer in such laminates. Nonwovens may be formed by various techniques, many of which may have drawbacks with respect to forming laminates. For instance, nonwoven webs made of carded staple fibers are typically softer and easily extensible, offering little resistance during mechanical activation, but said carded nonwovens are expensive and have lower tensile strength at break. On the other hand, spunbond nonwovens are relatively inexpensive but tend to be more rough in texture and therefore less preferable to consumers. The use of softer nonwovens to improve the feel often results in lower performance of the laminate. Indeed, there is often an inverse relationship between the strength of a laminate and its softness. While crimped spunbond fiber nonwovens have been proposed as enhancing softness while maintaining strength, crimping fibers involves additional steps and costs.

Therefore, there is a need for a laminate that includes a nonwoven having desirable softness and texture while maintaining suitable strength. There is a further need for reducing costs and increasing efficiency in creating elastomeric laminates.

SUMMARY OF THE INVENTION

An absorbent article includes a first waist region, a second waist region, and a crotch region disposed between the first and second waist regions. The article also includes a chassis having a topsheet, a backsheet, and an absorbent core disposed between the topsheet and backsheet; and an ear joined to the chassis. The ear may comprise a laminate formed from a first nonwoven and second nonwoven and an elastomeric material sandwiched between said first and second nonwovens. The laminate may further include a plurality of ultrasonic bonds; and the first nonwoven may comprise a noncrimped spunbond nonwoven web.

In further aspects, the first nonwoven may comprise an exterior surface having an average TS750 value of 5 db V2rms or less. Additionally or alternatively, the web may comprise an average bond area of 12% or less and/or an Average Normalized Peak Force of at least 0.160 (N/cm)/(g/m$^2$).

These and other features are described in more detail below.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 5 is a schematic, exploded illustration of an exemplary elastomeric laminate in accordance with the present invention;

FIG. 6 is a schematic plan view of an exemplary ear shape according to one nonlimiting embodiment of the present invention;

FIG. 6A is a schematic cross sectional view of the ear in FIG. 6 taken along the ear's lateral centerline;

DETAILED DESCRIPTION OF THE INVENTION

Figure 1A:
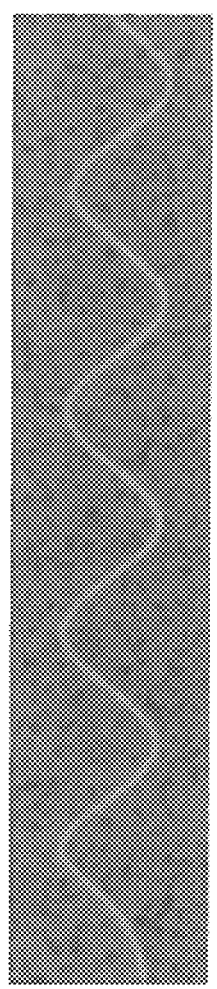
FIG. 1A is a photograph showing a crimped fiber.

"Activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation process can be applied to single substrate or laminate comprising multiple layers. Activation processes are disclosed for example in U.S. Pat. Pub. No. 2013/0082418, U.S. Pat. Nos. 5,167,897 and 5,993,432. "Activated" refers to a material that has been subjected to activation.

A "ring-rolled" or "ring-rolled activated" component has been activated by a ring-rolling system as is described U.S. Pat. Nos. 5,156,793 or 5,167,897 or by a High Speed Research Press (HSRP) as described in U.S. Pat. Nos. 7,062,983 and 6,843,134 issued to Anderson et al.

"Bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement.

"Bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multi-constituent components.

"Elastic," "elastomeric," and "elastically extensible" mean the ability of a material to stretch by at least 100% without rupture or breakage at a given load, and upon release of the load the elastic material or component exhibits at least 80% recovery (i.e., has less than 20% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Machine direction" or "MD" is the direction parallel to the direction of travel of the web in a manufacturing process. The machine direction is typically the longitudinal direction of a component, such as the ear of an absorbent article. The "cross machine direction" or "CD" is the direction substantially perpendicular to the MD and in the plane generally defined by the web.

"Nonwoven web" refers to a web having a structure of individual fibers or threads which are interlaid, but not in a repeating pattern as in a woven or knitted fabric, which do not typically have randomly oriented fibers. The basis weight of nonwoven fabrics is usually expressed in grams per square meter (gsm). The basis weight of a nonwoven web is the combined basis weight of the constituent layers and any other added components. Fiber diameters are usually expressed in microns; fiber size can also be expressed in denier, which is a unit of weight per length of fiber.

"Spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 8 and 40 microns.

A spunbond web may comprise crimped fibers or may be void of crimped fibers.

Figure 1B:
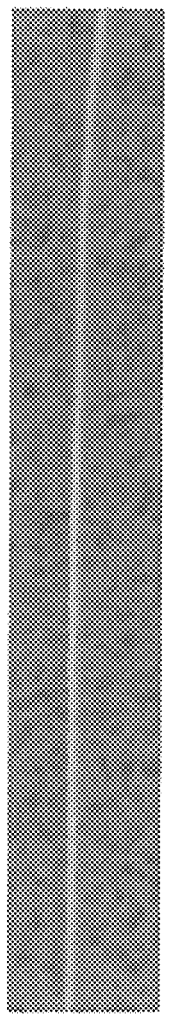
FIG. 1B is a photograph showing a straight fiber.

"Crimped fibers" or "crimped spunbond fibers" refers to bi-component spunbond fibers having a crimp, which fibers may be configured in a side-by-side, core-eccentric sheath or other suitable configuration. The selection of suitable resin combinations and bi-component fiber configuration can lead to a helical crimp or curl generated in the fibers. "Crimp" refers to the undulation, curling, or waves in a fiber. FIG. 1A is a photograph of a crimped spunbond fiber, while FIG. 1B is a photograph of a straight, noncrimped fiber. The crimp may occur spontaneously during the spinning or laydown process, on its own after web formation. In some instances, crimp may be induced mechanically or chemically during fiber making or processing. Crimping may be helical, planar, or combination of the two. The purpose of crimping fibers is to increase the volume per fiber, which in turn helps improve softness of the substrate made with crimped fibers. Microscopic or SEM analysis is often used to evaluate whether fibers have a crimped.

"Noncrimped" means the web that is substantially void of crimped spunbond fibers.

The Web

Figure 1C:
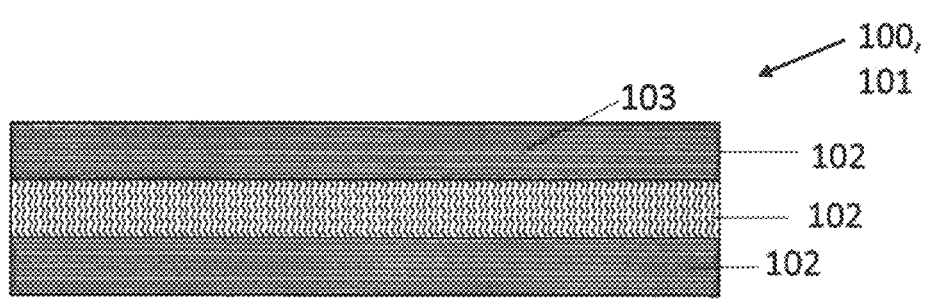
FIG. 1C is a schematic representation of a nonwoven laminate of the present invention shown in an cross sectional view of the nonwoven laminate.

The present invention relates to spunbond nonwoven webs 100 that are suitable for uses in an absorbent article, such as a disposable absorbent articles. Although shown to be rectangular in FIG. 1C, it is to be understood that the web is fibrous rather than smooth but is generally planar. The web may comprise a noncrimped spunbond nonwoven web. Noncrimped spunbond webs 101 comprise one or more layers 102 of noncrimped spunbond fibers 103. In some nonlimiting examples, the majority of layers in a noncrimped spunbond web comprises noncrimped spunbond layers. In some embodiments, the nonwoven web 100 is exclusively noncrimped spunbond layers.

In other aspects, the web 100 may comprise multiple layers 102 such as one or more layers having noncrimped spunbonds layer and one or more layers formed by other methods (e.g., meltblown, carded, through air bonded or hydroentangled fiber layers). Nonwoven layers 102 may comprise spunbond layers (S), nanofiber layers (N) and/or meltblown layers (M), and web may comprise any suitable configuration including but not limited to: SMS, SSS, SSMMS, SSMS, and SSMNMS. The web 100 may be void of carded fiber layers and/or void of crimped spunbond fiber layers.

Figure 2:
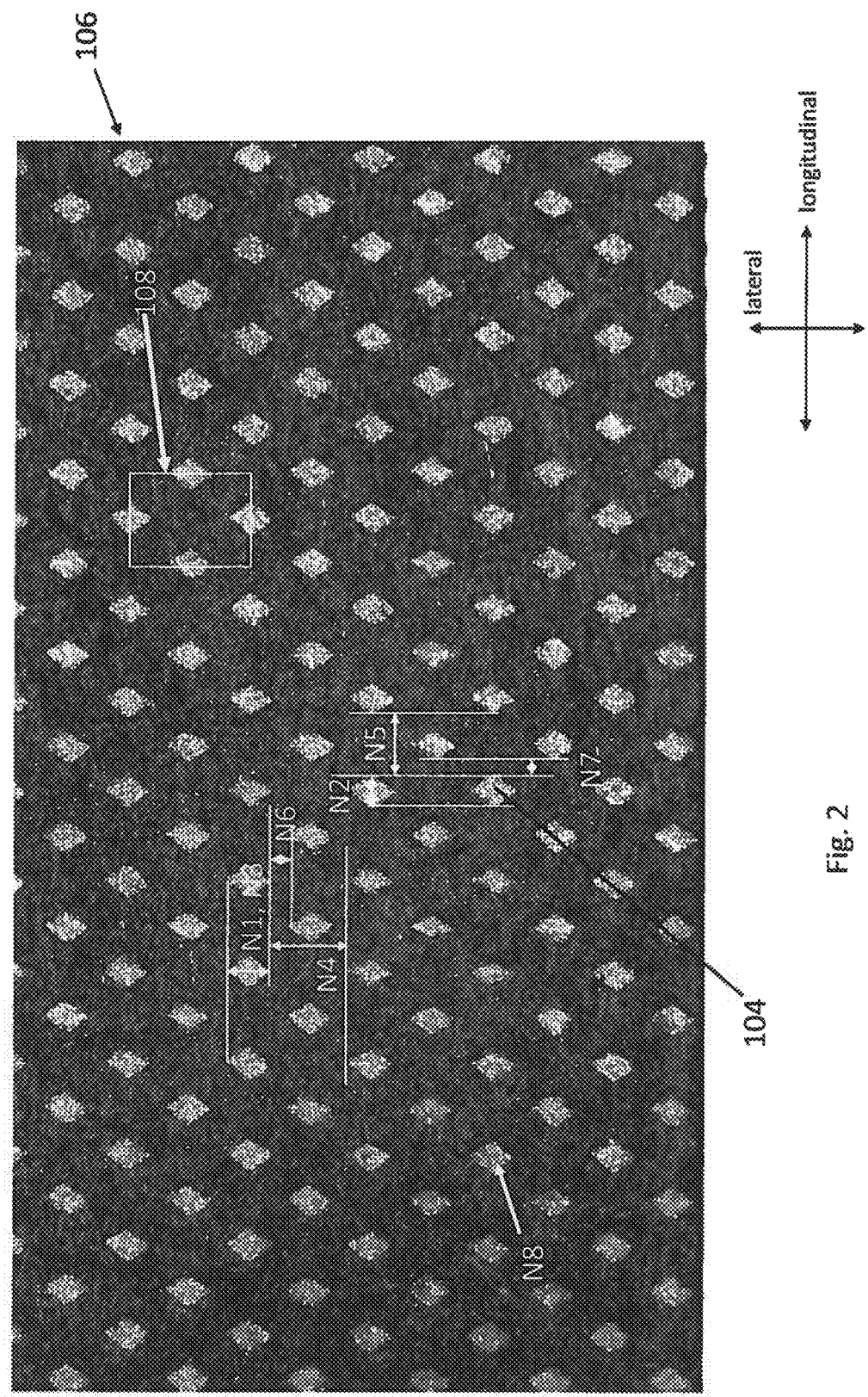
FIG. 2 is a photograph of an exemplary nonwoven and bond pattern.

The web's fiber layers may be joined by any suitable means, including calendaring bonding. The layers may be joined by a plurality of bonds 104 as shown in FIG. 2. In some embodiments, the web comprises an Average Bond Area Percentage of about 14% or less, or about 12% or less, or about 11.5% or less, or from about 5% to about 15%, or from about 7% to about 14%, or from about 8% to about 12%, reciting for each range every 1% increment therein, as determined by the Bond Dimensions Test Method herein.

The bonds 104 may comprise any suitable shape. In nonlimiting examples, the bonds are circular, elliptical, oval, rings, rods and combinations thereof. The bonds may comprise one or more curvilinear portions. Bonds within the plurality may comprise the same shape or different shapes. Likewise, bonds may comprise the same size or different sizes. In some embodiments, the web may comprise a bond pattern 106 that comprises one or more repeating units 108 as shown for example in FIGS. 2-4. The repeat unit is a portion of the pattern that can be replicated to create the entire pattern.

A bond may comprise a bond height (N2), which is the distance between its extremities in the longitudinal direction. In nonlimiting examples such those of FIGS. 3 and 4, the bond height may be at least 0.35 mm, or at least 0.75 mm, or at least 1 mm, or at least 1.25 mm, or at least 1.5 mm, or at least 2 mm, or at least 3 mm, or from about 0.45 mm to about 10 mm, or from about 1 mm to about 8 mm, reciting for each range every 0.1 mm increment therein. Additionally or alternatively, the nonwoven may comprise an Average Bond Height ($N2_{av}$) of at least 0.35 mm, or at least 0.75 mm, or at least 1 mm, or at least 1.25 mm, or at least 1.5 mm, or at least 2 mm, or at least 3 mm, or from about 0.45 mm to about 10 mm, or from about 1 mm to about 8 mm, reciting for each range every 0.1 mm increment therein. A bond further comprises a bond width (N1), which is the distance between its extremities in the lateral direction. The bond width may be greater than or less than the bond height for the given bond. Alternatively, the bond width may be approximately the same as the bond height. In nonlimiting examples, the bond width may be at least 1.25 mm, or at least 1.5 mm, or at least 2 mm, or at least 2.15 mm. Additionally or alternatively, the nonwoven may comprise an Average Bond Width ($N1_{av}$) of at least 1.25 mm, or at least 1.5 mm, or at least 2 mm, or at least 2.15 mm. In some embodiments shown in FIGS. 3 and 4, a bond may comprise a major dimension (i.e., the greatest dimension in any direction) of at least 1.25 mm, or at least 1.5 mm, or at least 1.75 mm, or at least 2 mm, or at least 2.15 mm, or at least 3 mm or from about 1.25 to about 8 mm, reciting for said range every 0.1 mm increment therein. The major dimension may be the height or the width, or may extend in a direction that is disposed at an angle with respect to the longitudinal and lateral directions. Additionally or alternatively, the web may comprise an average bond major dimension of at least 1.25 mm, or at least 1.5 mm, or at least 1.75 mm.

Figure 3:
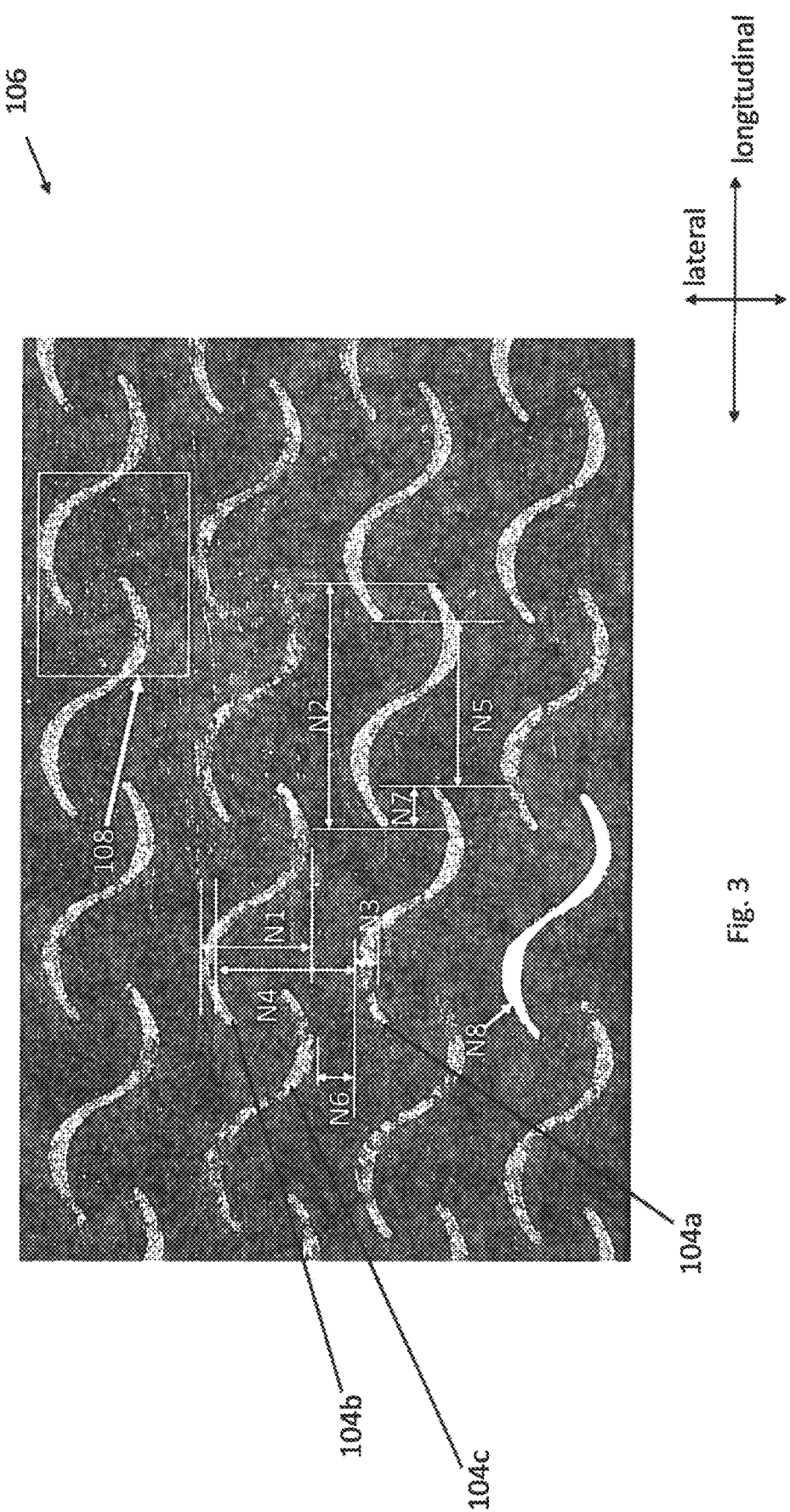
FIG. 3 is a photograph of an exemplary nonwoven and bond pattern.

The bond also comprises a bond thickness (N3) which is the maximum lateral thickness of the bond. In some nonlimiting examples, the bond height is the same as the bond thickness as can be seen for example in FIG. 4. However, in other examples, the thickness of the bond differs from the bond height as shown in FIG. 3. The bond thickness (N3) may be at least 0.5, or at least 0.75 mm, or at least 1 mm, or at least 1.25 mm, or at least 1.5 mm, or at least 2 mm, or at least 2.15 mm, or from about 0.5 mm to about 3 mm, or from about 0.75 mm to about 2.25 mm, reciting for each range every 0.1 mm increment therein. The web may comprise an Average Bond Thickness ($N3_{av}$) may be at least 0.5, or at least 0.75 mm, or at least 1 mm, or at least 1.25 mm, or at least 1.5 mm, or at least 2 mm, or at least 2.15 mm, or from about 0.5 mm to about 3 mm, or from about 0.75 mm to about 2.25 mm, reciting for each range every 0.1 mm increment therein.

Each bond further comprises a bond site area (N8), which is the two dimensional area of the bond. In certain embodiments, the bond site area is at least about 0.5 $mm^2$, or at least about 0.6 $mm^2$, or at least about 0.75 $mm^2$, or from about 0.5 $mm^2$ to about 2 $mm^2$, reciting for said range every 0.1 $mm^2$ increment therein. The nonwoven web may comprise an Average Bond Site Area ($N8_{av}$) of at least about 0.5 $mm^2$, or at least about 0.6 $mm^2$, or at least about 0.75 $mm^2$, or from about 0.5 $mm^2$ to about 2 $mm^2$, reciting for said range every 0.1 $mm^2$ increment therein. The bond height, bond width, bond thickness, bond site area and the bond area percentage and the average of the each can be determined by the Bond Dimensions Test Method herein.

The spacing between bonds may be the same or may vary at different areas of the web. The web may comprise overlapping bonds and/or staggered bond patterns. The bonds may be arranged such that one or more rows and/or columns of bonds are formed, as can be seen for example in FIGS. 2-4. The columns may be longitudinally extending and the rows may be laterally extending. Two laterally adjacent, nonoverlapping bonds may comprise a Minimum Lateral Bond Distance (N4) of at least about 2.25 mm, or at least about 2.5 mm, or at least about 3 mm, or at least about 3.5 mm, or from about 2.25 mm to about 5 mm, or from about 2.5 to about 4 mm, or from about 3 to about 3.75 mm, reciting for each range every 0.5 mm increment therein, as measured by the Bond Dimensions Test Method herein. As shown in FIG. 3, by adjacent, nonoverlapping, it is meant that the bonds have no bonds 104a, 104b between them in the direction of measurement when ignoring any overlapping bonds (such as 104c). The web may comprise an Average Minimum Lateral Bond Distance ($N4_{av}$) of at least about 2.25 mm, or at least about 2.5 mm, or at least about 3 mm, or at least about 3.5 mm, or from about 2.25 mm to about 5 mm, or from about 2.5 to about 4 mm, or from about 3 to about 3.75 mm, reciting for each range every 0.1 mm increment therein, as measured by the Bond Dimensions Test Method herein.

Two adjacent columns may comprise a Minimum Lateral Column Offset (N6) of at least about 0.3 mm, or at least about 0.5 mm, or at least about 1 mm, or from about 0.3 mm to about 2 mm, or from about 0.5 to about 1.5 mm, reciting for each range every 0.1 mm increment therein. Additionally or alternatively, the web may comprise an Average Minimum Lateral Column Offset ($N6_{av}$) at least about 0.3 mm, or at least about 0.5 mm, or at least about 1 mm, or from about 0.3 mm to about 2 mm, or from about 0.5 to about 1.5 mm, reciting for each range every 0.1 mm increment therein.

Two longitudinally adjacent, nonoverlapping bonds may comprise a Minimum Longitudinal Bond Distance (N5) of at least about 1.5 mm, or at least about 2 mm, or at least about 3 mm, or at least about 3.5 mm, or from about 1.4 mm to about 6 mm, or from about 2 mm to about 5 mm, or from about 3 to about 4.75 mm, reciting for each range every 0.1 increment therein. Additionally or alternatively, the web may comprise an Average Minimum Longitudinal Bond Distance ($N5_{av}$) of at least about 1.5 mm, or at least about 2 mm, or at least about 3 mm, or at least about 3.5 mm, or from about 1.4 mm to about 6 mm, or from about 2 mm to about 5 mm, or from about 3 to about 4.75 mm, reciting for each range every 0.1 increment therein.

Two adjacent rows may comprise a Minimum Longitudinal Row Offset (N7) of at least about 1.05 mm, or at least about 1.1 mm, or from about 1 mm to about 2 mm, or from about 1.1 to about 1.6 mm, reciting for each range every 0.5 mm increment therein. Additionally or alternatively, the web may comprise an Average Minimum Longitudinal Row Offset ($N7_{av}$) of at least about 1.05 mm, or at least about 1.1 mm, or from about 1 mm to about 2 mm, or from about 1.1 to about 1.6 mm, reciting for each range every 0.5 mm increment therein.

For the avoidance of doubt, bond distances and row or column distances can be taken from different adjacent bonds. In other words, the nearest adjacent, nonoverlapping bond may not be in the nearest row or column. In the case of a staggered pattern as shown in FIG. 3 for example, the Minimum Lateral Bond Distance (N4) is taken between a first bond 104a and the nearest, yet nonoverlapping bond 104b, while the Minimum Lateral Column Offset (N6) is taken between the first bond 104a and its nearest adjacent bond in the lateral direction 104c.

Figure 4:
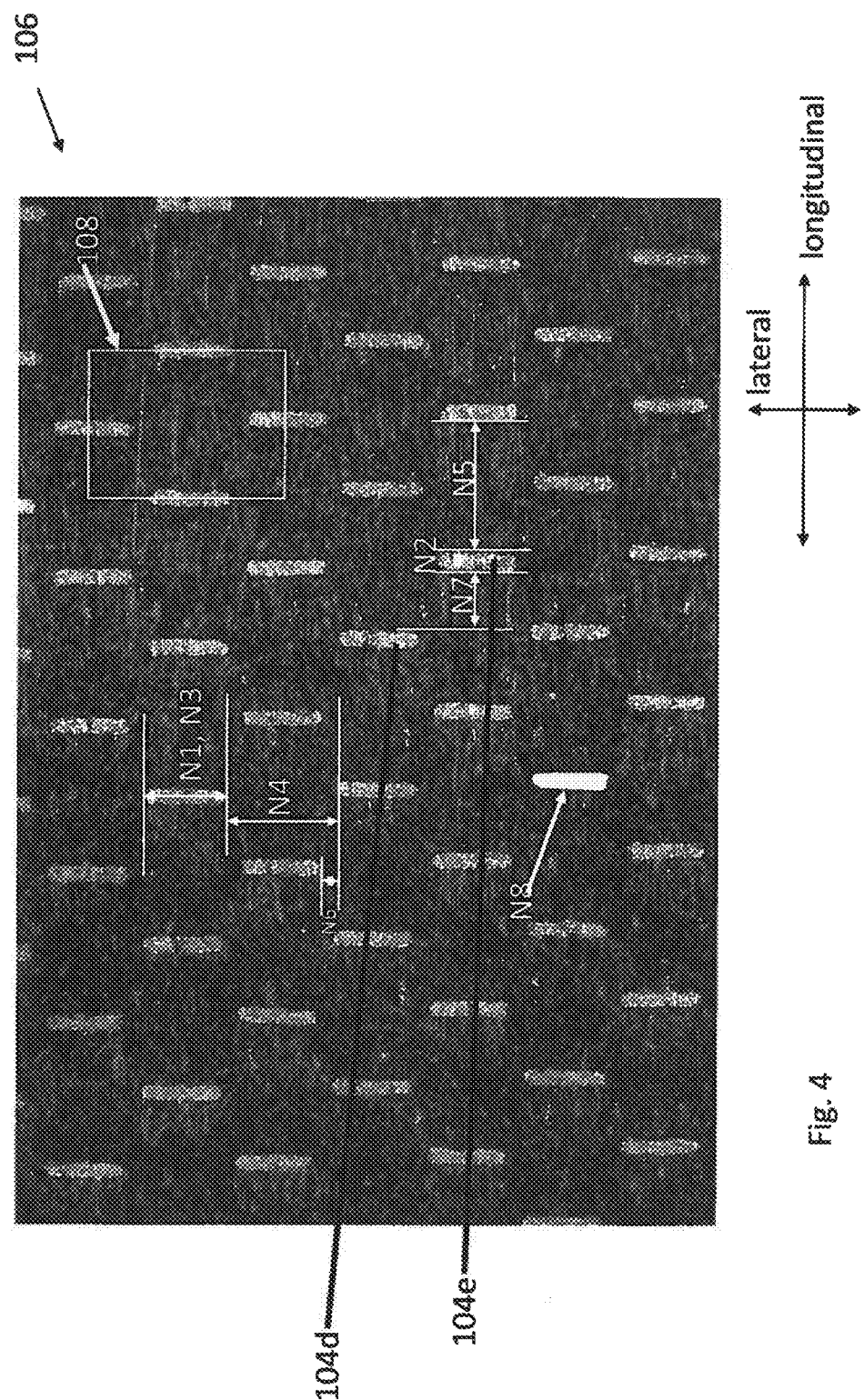
FIG. 4 is a photograph of an exemplary nonwoven and bond pattern.

Further, because the plurality of bonds may comprise overlapping portions, it is within the scope of the invention that the distances may be measured "forward" as shown for example with N7 in FIG. 4 from a right edge of a first bond 104d to a left edge of a bond in the adjacent column 104e, or "backward" as shown for example with N7 in FIG. 3 from a right edge of a first bond 104d to a left edge of a bond in the adjacent column 104e (where the bonds overlap). Positive numbers will be used to express the measurement regardless whether the bonds are overlapping.

Suitable noncrimped spunbond nonwoven webs may comprise an Average % Strain at Peak Force of about 70% or less, or from about 40% to about 60%, reciting for each range every 1% increment therein, according to the Tensile Test Method herein. Additionally or alternatively, the nonwoven web may comprise an Average Normalized Peak force of at least about 0.150 (N/cm)/(g/m$^2$), or at least about 0.160 (N/cm)/(g/m$^2$), or from about 0.160 (N/cm)/(g/m$^2$) to 0.230 (N/cm)/(g/m$^2$).

As shown in FIG. 5, a web 100 may comprise an opposing surfaces 314, 316, which are disclosed further below. In certain embodiments, the web may comprise one or more surfaces with an Average TS750 value of about 11 dB V$^2$ rms or less, or about 10 dB V$^2$ rms or less, or about 5 dB V$^2$ rms or less, or from about 1 dB V$^2$ rms to about 11 dB V$^2$ rms, or from about 1.5 dB V$^2$ rms to about 6 dB V$^2$ rms, or from about 2 dB V$^2$ rms to about 4 dB V$^2$ rms according to the Softness Test Method herein, reciting for each range every 0.1 dB V$^2$ rms increment therein. Additionally or alternatively, the web comprises one or more surfaces which comprise an Average TS7 value of about 7 dB V$^2$ rms or less, or about 6.5 dB V$^2$ rms or less, or about 6.4 or less, or from about 1 dB V$^2$ rms to about 7 dB V$^2$ rms, or from about 4 dB V$^2$ rms to about 6.5 dB V$^2$ rms according to the Softness Test Method herein, reciting for each range every 0.1 dB V$^2$ rms increment therein. Lower TS7 and TS750 values indicate greater softness, which is highly desirable in absorbent articles. Consumers might find absorbent articles with high TS7 and TS750 values uncomfortable and/or scratchy or otherwise undesirable.

In some nonlimiting examples, the nonwoven web 100 comprises a basis weight of about 25 gsm or less, or about 17 gsm or less, or about 14 gsm or less, or from about 10 gsm to about 25 gsm.

Elastomeric Laminate Incorporating the Web

Figure 6B:
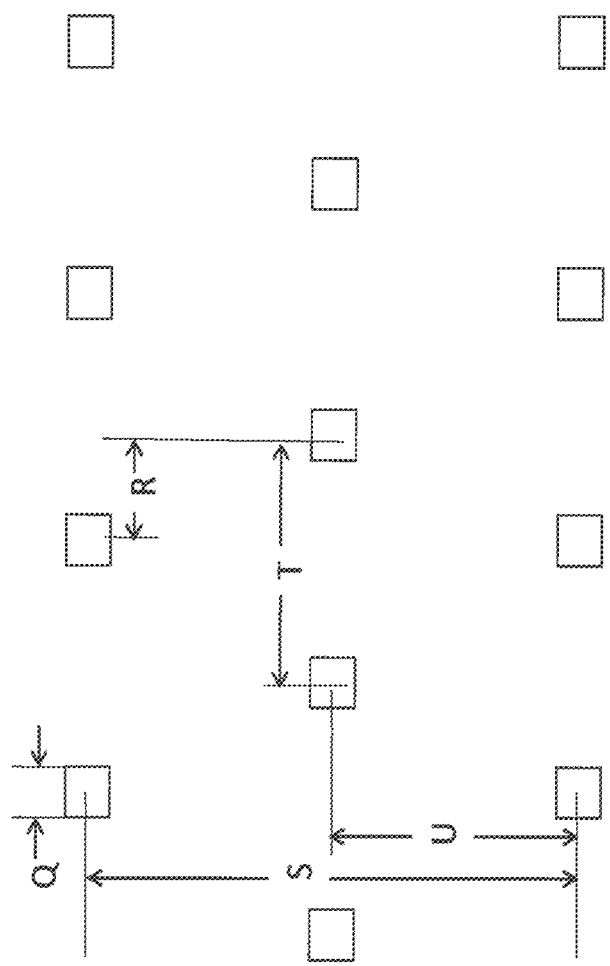
FIG. 6B is a schematic plan view of an exemplary ultrasonic bond pattern.

FIG. 5 schematically depicts an exemplary elastomeric laminate 310 that comprises a noncrimped spunbond nonwoven web 100. In the example shown in FIG. 6, an ear 30 of an absorbent article comprises the elastomeric laminate. It is also contemplated that other components of an absorbent article may comprise the elastomeric laminate such as waist bands, belts, and/or leg cuffs.

The elastomeric laminate may comprise a first nonwoven web 300 and an elastomeric layer 302. The first nonwoven web 300 may comprise one or more layers 102 comprising noncrimped spunbond fibers 103, having any of the features described above and illustrated in FIG. 1C. Returning to FIG. 5, the first nonwoven web 300 may comprise additional layers such as meltblown and/or nanofiber layers. In nonlimiting examples, the first nonwoven web 300 is void of carded and/or crimped spunbond fiber layers. The nonwoven web 300 may comprise a first external surface 314 and a first interior surface 316. The first interior surface 316 is substantially opposite the first external surface and faces the elastomeric layer 302. In certain embodiments, a noncrimped spunbond fiber nonwoven web 100 forms the external surface 314.

The elastomeric layer may comprise one or more elastomeric materials which provide elasticity to at least a portion of said layer. Nonlimiting examples of elastomeric materials include film (e.g., styrenic block copolymer film, elastomeric polyolefin films, polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives, polyesters, polyurethanes, polyether amides, polyolefins, combinations thereof or any suitable known elastomers. Exemplary elastomers and/or elastomeric materials are disclosed in U.S. Pat. Nos. 8,618, 350; 6,410,129; 7,819,853; 8,795,809; 7,806,883; 6,677, 258, 9,834,667, and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.), VERSIFY (homopolyolefins and random copolymers, and blends of random copolymers, available from Dow Chemical Company, Midland, Mich.), TAFMER (polyolefin elastomer available from Mitsui Chemicals), and INFUSE (olefin block copolymer, available from Dow Chemical, Midland Mich.).

In nonlimiting examples, the elastomeric layer comprises a film. The film may comprise a single layer or multiple layers. The film may be preactivated or unactivated. The film may be elastic in one or more directions. For example when incorporated into an absorbent article, the film may be elastic in the lateral and/or longitudinal direction of the article. The elastomeric layer may comprise a width, Y, as shown for example in FIG. 6. (FIG. 6 depicts an ear 30 which comprises an elastomeric laminate.) In some embodiments, Y is less than the width, W, of the laminate by at least about 10 mm. The elastomeric layer may have a length dimension that is the same as the laminate's length along with the entire width of the elastomeric layer, or a length dimension that is less than the length of the laminate at any point along with the width of the second layer. In some embodiments, the elastomeric layer may have a basis weight of from about 5 to about 150 gsm, or from about 10 to about 100 gsm, or less than about 150 gsm, reciting for each range every 1 gsm increment therein.

As also illustrated in FIG. 6, the laminate may comprise an elastic region 306. The elastic region 306 is generally defined by the perimeter of the elastomeric material. In the elastic region, the laminate is elastically extensible. In some embodiments, for example when an ear 30 comprises the laminate, the area of the elastic region comprises at least about 20% of, or from about 30% to about 80% of the total area of the laminate, reciting for said range every 5% increment therein. In further embodiments, Y (i.e., the maximum width of the elastomeric layer) is at least about 20% of, or from about 25% to about 85%, or from about 35% to about 80% of the total width, W, of the laminate, reciting for each range every 5% increment therein. The laminate further comprises one or more inelastic regions. In certain embodiments, the laminate comprises a first inelastic region 308, which extends laterally outward from the proximal edge 38 and is adjacent to the elastic region 306 at a first elastomeric material edge 307. The laminate may further include a second inelastic region 312, which may extend laterally inward from the distal side 36 and may be adjacent to the elastic region 306 at a second elastomeric material edge 309. The first and second inelastic regions may be made of the same material(s) or different materials.

The elastomeric laminate may further comprises a second nonwoven web 304. The elastomeric layer 302 may be sandwiched between the first and second nonwoven layers 300, 304. The second nonwoven web may comprise one or more nonwoven layers 102 which may include spunbond layers, nanofiber layers and/or meltblown layers. The second nonwoven web may comprise a noncrimped spunbond fiber web 100', having any of the features described with respect to noncrimped webs 100 above. Alternatively, the second nonwoven web may be void of noncrimped spunbond fiber fibers. In nonlimiting examples, the second nonwoven web 304 is void of carded and/or crimped spunbond fiber layers. The second nonwoven web 304 may comprise a second external surface 318 and a second interior surface 320. The second interior surface 320 is substantially opposite the second external surface and faces the elastomeric layer 302. In certain embodiments, a noncrimped spunbond fiber nonwoven web 100' forms the external surface 318.

In certain embodiments, the elastomeric laminate comprises a gathered laminate, wherein one of the layers is strained to a greater degree than a remaining layer during lamination. In this way, the relatively less extensible layer (i.e., the nonwoven) will form gathers when the laminate is in a relaxed state. In some embodiments, at least a portion of the elastomeric layer is strained while the nonwoven web(s) is/are in a relaxed state during lamination. The elastomeric layer may be stretched one or more directions. Corrugations then form in the nonwoven web(s) when the subsequently formed laminate is in a relaxed state. In nonlimiting examples, the elastomeric layer is stretched in a direction corresponding with the lateral direction of the article. In other words, when the laminate is joined to the chassis subsequent to lamination, it will be oriented such that the laminate is stretchable and/or elastic in the lateral direction of the article. In further nonlimiting examples, the laminate is also stretchable and/or elastic in the longitudinal direction.

The laminate layers may be joined by any suitable means. In some nonlimiting examples, the elastomeric layer is joined to the first and/or second nonwoven layers by a plurality of ultrasonic bonds.

In certain embodiments, the elastomeric laminate 310 may comprise an Air Permeability Value of at least about 1 $m^3/m^2/min$, or from about 1 $m^3/m^2/min$ to about 125 $m^3/m^2/min$, or from about 1 $m^3/m^2/min$ to about 35 $m^3/m^2/min$ according to the Air Permeability Test Method herein, reciting for each range every 1 $m^3/m^2/min$ increment therein.

Figure 8:
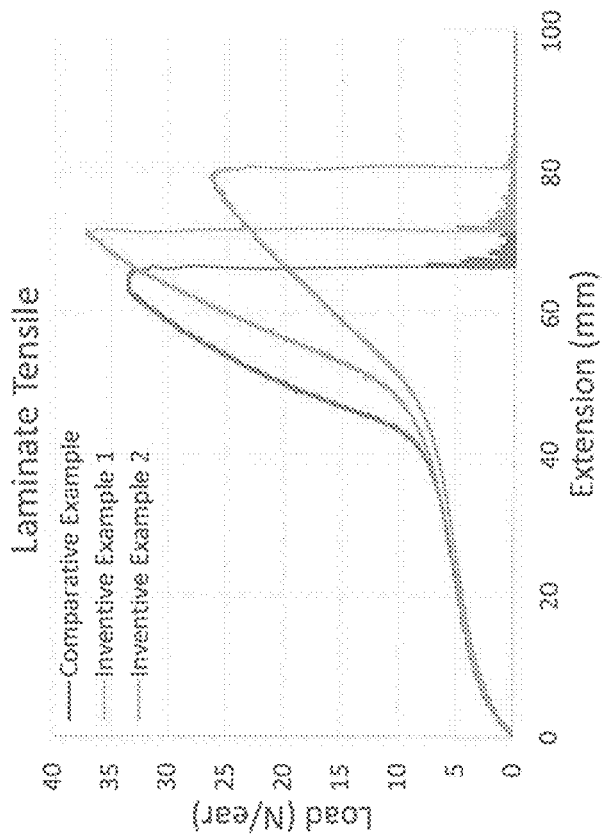
FIG. 8 is a chart depicting extensibility characteristics of exemplary laminates.

In further embodiments, the elastomeric laminate may comprise an Average Load at Break of about 25N or greater, or from about 25N to about 40N according to the Tensile Test Method herein. The laminate may comprise an Average Extension at Load at Break of about 65 mm or greater, or 70 mm about or greater, or from about 65 mm to about 85 mm, or from about 70 mm to about 80 mm according to the Tensile Test Method herein. The laminate may fail within 50 mm once load crosses 10N value, as shown in FIG. 8.

In various embodiments, the elastomeric laminate may comprise one or more surfaces in the elastic region 306 with an Average TS750 value of about 115 dB $V^2$ rms or less, or about 100 dB $V^2$ rms or less, or about 90 dB $V^2$ rms or less, or from about 50 dB $V^2$ rms to about 115 dB $V^2$ rms, or from about 60 dB $V^2$ rms to about 90 dB $V^2$ rms according to the Softness Test Method herein, reciting for each range every 1 dB $V^2$ rms increment therein. The elastomeric laminate may comprise on or more surfaces in an inelastic region 308, 312 with an Average TS750 value of about 22 dB $V^2$ rms or less, or about 10 dB $V^2$ rms or less, or about 9 dB $V^2$ rms or less, or from about 2 dB $V^2$ rms to about 22 dB $V^2$ rms, or from about 6 dB $V^2$ rms to about 10 dB $V^2$ rms according to the Softness Test Method herein, reciting for each range every 1 dB $V^2$ rms increment therein.

Additionally or alternatively, the elastomeric laminates of the present invention may comprise one or more surfaces in the elastic region 306 which comprise an Average TS7 value of about 15 dB $V^2$ rms or less, or about 12 dB $V^2$ rms or less, or from about 5 dB $V^2$ rms to about 15 dB $V^2$ rms, or from about 8 dB $V^2$ rms to about 12 dB $V^2$ rms according to the Softness Test Method herein, reciting for each range every 1 dB $V^2$ rms increment therein. The elastomeric laminates of the present invention may comprise one or more surfaces in an inelastic region 308 which comprise an Average TS7 value of about 6 dB $V^2$ rms or less, or about 5.6 dB $V^2$ rms or less, or from about 3 dB $V^2$ rms to about 6 dB $V^2$ rms, or from about 4 dB $V^2$ rms to about 5.6 dB $V^2$ rms according to the Softness Test Method herein, reciting for each range every 1 dB $V^2$ rms increment therein. Lower TS7 and TS750 values indicate greater softness, which is highly desirable in absorbent articles. Consumers might find absorbent articles with high TS7 and TS750 values uncomfortable and/or scratchy or otherwise undesirable.

The first and/or the second external surface may comprise any of the TS7 and/or TS750 values disclosed herein. In various embodiments, the laminate is free of carded and/or crimped spunbond nonwoven webs.

EXAMPLES

Table 1 below shows a comparison of nonwoven materials that may be utilized in elastomeric laminates. Nonwoven Example 1 includes a nonwoven that is available from Avgol, USA under tradename AVMN1073333001. The nonwoven is made of polypropylene and additives, and is having an average basis weight of 17.2±1 gsm as measured by the Basis Weight Test Method herein. The nonwoven has SMS structure, i.e. has three layers spunbond, meltblown, spunbond respectively. The nonwoven is thermally bonded and has "diamond" shape bond pattern as shown in FIG. 2. The bond dimensions are listed below in Table 1.

Nonwoven Example 2 includes a nonwoven that is available from Avgol, USA under tradename AVMN1083134001. The nonwoven is made of polypropylene and additives, and is having an average basis weight of 16.87±0.3 gsm as measured by the Basis Weight Test Method herein. The nonwoven has SSS structure, i.e. has three layers spunbond, spunbond, spunbond respectively. The nonwoven is thermally bonded and has "S" shape bond pattern as shown in FIG. 3. The bond dimensions are listed below in Table 1.

Nonwoven Example 3 includes a nonwoven that is available from Fitesa, Germany under tradename SS6XX-99. The nonwoven is made of polypropylene and additives, and is having an average basis weight of 16.2±0.4 gsm as measured by the Basis Weight Test Method herein. The nonwoven has SSS structure, i.e. has three layers spunbond, spunbond, spunbond respectively. The nonwoven is thermally bonded and has "rod" shape bond pattern as shown in FIG. 4. The bond dimensions are listed below in Table 1.

TABLE 1

Nonwoven Bond Dimensions

| | Nonwoven Example 1 | Nonwoven Example 2 | Nonwoven Example 3 |
|---|---|---|---|
| Average Bond CD Width (mm) ($N1_{av}$) | 1.16 | 3.41 | 2.18 |
| Average Bond MD Height (mm) ($N2_{av}$) | 0.69 | 7.03 | 0.41 |
| Average Max CD Bond thickness (mm) ($N3_{av}$) | 1.16 | 0.58 | 2.18 |
| Average Minimum Lateral Bond Distance (mm) ($N4_{av}$) | 2.16 | 3.68 | 3.1 |
| Average Minimum Longitudinal Bond Distance (mm) ($N5_{av}$) | 1.33 | 4.73 | 3.52 |
| Average Minimum Lateral Column Offset (mm) ($N6_{av}$) | 0.49 | 1.19 | 0.37 |
| Average Minimum Longitudinal Row Offset (mm) ($N7_{av}$) | 1.01 | 1.15 | 1.51 |
| Single Bond Site/Shape Area ($mm^2$) ($N8_{av}$) | 0.48 | 3.35 | 0.9 |
| Average Bond Area Percentage (%) | 15.07 | 11.34 | 8.45 |

Figure 7:
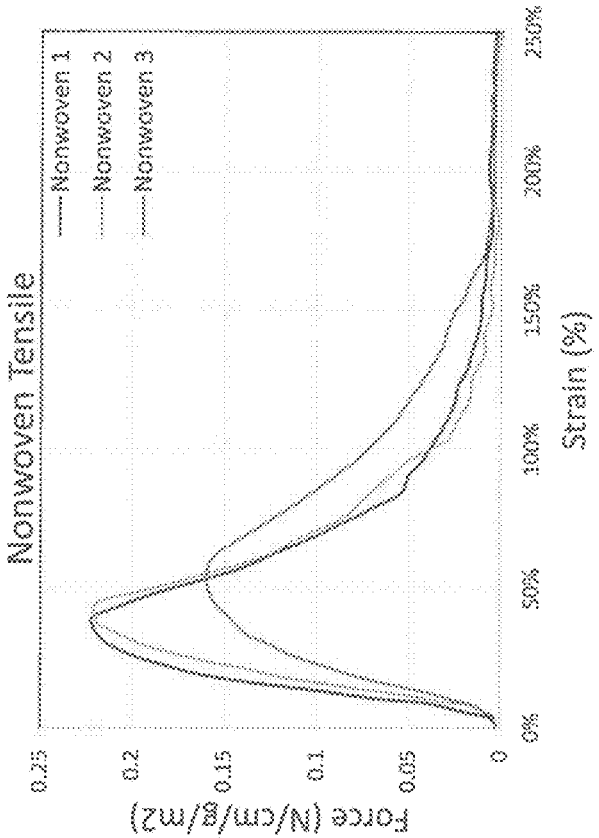
FIG. 7 is a chart depicting tensile properties of exemplary nonwoven webs.

Table 2 and FIG. 7 show a comparison of the tensile properties of the nonwoven examples. As can be seen in Table 2 and FIG. 7, Nonwoven Examples 2-3 have an Average Normalized Peak Force higher than 0.16 (N/cm)/($g/m^2$) and equal or greater Average % Strain at Peak Force than the comparative nonwoven spunbond example. Typically, such high normalized peak force is harder to achieve with softer spunbond nonwoven. The use of nonwoven webs having the properties of Nonwoven Example 2 and/or Nonwoven Example 3 help deliver desirable elastic laminate properties for absorbent article comfort and conforming fit.

TABLE 2

Nonwoven Tensile Data

| Example | Average Normalized Peak Force | Average % Strain at Peak Force |
|---|---|---|
| Nonwoven Example 1 | 0.233 ± 0.014 N/cm/$g/m^2$ | 38.0 ± 1.0% Strain |
| Nonwoven Example 2 | 0.229 ± 0.008 N/cm/$g/m^2$ | 41.5 ± 3.1% Strain |
| Nonwoven Example 3 | 0.162 ± 0.020 N/cm/$g/m^2$ | 54.4 ± 6.3% Strain |

Examples of Ear Laminates

Comparative Laminate Example A includes a first nonwoven and second nonwoven, and an elastomeric film sandwiched between the first and second nonwoven. Each of the first and second nonwoven are Nonwoven Example 1 above in approximately 250 mm width. The elastomeric film is ElastiPro™4407 available from Clopay, USA and has a basis weight of 53.5±1.2 gsm. The film comprises a width of 45 mm in a relaxed condition. Said film was pre-activated using ring-roll machine to 210% strain at average strain rate of 500 $second^{-1}$ using 1.524 mm pitch teeth. The pre-activated film was stretched to overall 130% strain (i.e., 45 mm stretched to about 89 mm) on laminate making process as described in U.S. patent application Ser. No. 15/674,625. The 7 mm lateral ends of the film were not stretched; only the central section of 31 mm was stretched to 75 mm. The film width grew by 2-4 mm due to permanent set induced by the pre-activation and stretching steps. While the film was stretched as described, the first and second nonwoven were ultrasonically bonded through the film, using the bonding pattern shown in FIG. 2 and at an ultrasonic bond pressure of 500N. The first and second nonwoven webs were wider than the lateral width required for bonding the film. The film was bonded on the outside lateral ends of the laminate with outer edge of the film at least 25 mm away from the respective outer edge of the nonwovens as measured in the lateral direction; thereby producing an inelastic regions 308, 312 (i.e., area without film) and an elastic region 306 (i.e., area with film) in the laminate. In both the inelastic and elastic regions, the laminate layers were bonded with ultrasonic bonding using the pattern shown in FIG. 6B, wherein Q is 0.7 $mm^2$ and represents the area of the ultrasonic bond, R is 2.5 mm and represents the lateral off-set from bond center to bond center in adjacent longitudinal columns; S is 8 mm and represents the longitudinal spacing of adjacent, nonoverlapping ultrasonic bonds in the longitudinal direction, T is 5 mm and represents the lateral spacing of adjacent nonoverlapping ultrasonic bonds in the lateral direction from center to center, and U is 4 mm and represents the longitudinal offset from center to center in adjacent lateral rows.

Inventive Laminate Example 1 was made in the same manner as Comparative Laminate Example A above except the Nonwoven Example 2 was used as the first and second nonwovens.

Inventive Laminate Example 2 was made in the same manner as Comparative Laminate Example A above except the Nonwoven Example 3 was used as the first and second nonwovens.

Each of the exemplary ear laminates above are cut into specimens having the shapes with the dimension detailed below in Table 3. The dimensions are illustrated schematically and not to scale in FIG. 6. A die made with the shape is used to cut the specimen. The specimens are cut to have inelastic regions on both lateral sides of the elastic region. Specimens were cut with an inelastic region of at least about 10 mm as measured laterally inward from the outboard edge 36. In each shape, the first lateral side 40 intersects with the outboard edge 36 at a first corner 37 and the second lateral side 42 intersects with the inboard edge 38 at a second corner 39. The longitudinal distance, Loff, between said corners indicates the positioning of a fastening system (i.e., towards the top of the ear, middle of the ear etc.).

The exemplary specimens were tested to determine their Average Load at Break, and/or their Average Extension at Break using the Tensile Test Method herein. In such test, the outboard side of the specimen was mounted in the top grip at a position G1, located at the distance X indicated in Table 3 (which corresponds to an inboard edge 52a of the fastener attachment bond 52 (see FIG. 6A)). The bottom grip was mounted at a position, G2, at the gage length of 55 mm as per the Tensile Test Method.

TABLE 3

Laminate Shape Dimensions
In Table 3, lengths are measured along a line perpendicular to the lateral centerline 43 and widths are measured along a line parallel to the lateral centerline.

| Symbol | Description | Dimension |
|---|---|---|
| Li | Length of shape's inboard edge 38 | 101.6 mm |
| Lo | Length of shape's outboard edge 36 | 25.4 mm |
| W | Maximum width of shape | 65 mm |
| X | Maximum width between outboard edge 36 and first grip position G1 | 7 mm |
| Y | Maximum width of film | 49 mm |
| Z | Maximum width between first grip position G1 and outboard film edge 309 | 3 mm |
| α | Angle of slope of the first lateral side 40 | 30.38° |
| β | Angle of slope of the second lateral side 42 | 30.38° |
| Loff | Offset length between a first corner 37 on the outboard edge 36 and a second corner 39 on the inboard edge 38 | 38.1 mm |

The laminate shape is chosen to provide angles (a and (3) commonly used in diaper ear applications. The higher a and 13 angles translate into high stress intensification when ear is tested under tensile condition (as described in the methods below). The high stress intensification usually results in lower strength to break ears.

The laminates tested for softness and tensile properties as shown in the Tables below. Table 4 shows a comparison of softness values of the exemplary nonwovens, and Tables 5-6 show comparisons of the softness values of the exemplary laminates. The nonwovens used in the laminate were evaluated for softness using the Softness Test herein. Both surfaces of the nonwoven webs were evaluated for Average TS7 and TS750 values as shown in Table 4. As shown in the Table 4, the nonwoven examples tend to have similar average TS7 values, but Nonwoven Examples 2 and 3 have much lower average TS750 values compared to Nonwoven Example 1.

TABLE 4

Nonwoven Softness Data

| Nonwoven Example | Average TS7 | Average TS750 |
|---|---|---|
| Nonwoven Example 1 Surface A | 6.50 ± 0.45 | 13.17 ± 0.65 |
| Nonwoven Example 1 Surface B | 6.56 ± 0.24 | 12.02 ± 0.46 |
| Nonwoven Example 2 Surface A | 5.42 ± 0.28 | 3.57 ± 0.36 |

TABLE 4-continued

Nonwoven Softness Data

| Nonwoven Example | Average TS7 | Average TS750 |
|---|---|---|
| Nonwoven Example 2 Surface B | 6.37 ± 0.25 | 3.76 ± 0.35 |
| Nonwoven Example 3 Surface A | 5.13 ± 0.39 | 2.64 ± 0.24 |
| Nonwoven Example 3 Surface B | 6.78 ± 0.31 | 3.80 ± 0.46 |

Tables 5-6 show comparisons of the softness values of the exemplary laminates. The laminates were evaluated for softness in two different sections: the elastic section 306 and the inelastic section 308 (which consists of the two nonwovens laminated without elastic film therebetween). Inventive Laminate Examples 1 and 2 each showed lower Average TS7 values and drastically lower Average TS750 values. The unique process of forming ultrasonically bonded stretch laminates enables lowering the TS7 values, which is more prominently shown with Inventive Example 1. Further, the ultrasonic bonding laminate forming process did not affect the TS750 value trend observed for the nonwoven examples.

TABLE 5

Laminate Film Area Softness Data

| Laminate (Elastic Region) | TS7 | TS750 |
|---|---|---|
| Comparative Laminate Side A | 14.08 ± 2.19 | 123.33 ± 24.38 |
| Comparative Laminate Side B | 17.38 ± 2.54 | 121.21 ± 19.23 |
| Inventive Laminate 1 Side A | 9.17 ± 1.11 | 90.02 ± 15.42 |
| Inventive Laminate 1 Side B | 9.22 ± 0.78 | 61.63 ± 3.14 |
| Inventive Laminate 2 Side A | 12.00 ± 1.25 | 72.76 ± 12.29 |
| Inventive Laminate 2 Side B | 14.56 ± 0.49 | 75.04 ± 10.16 |

TABLE 6

Laminate NW Area Softness Data

| Laminate (inelastic region; nonwovens only) | TS7 | TS750 |
|---|---|---|
| Comparative Laminate Side A | 5.89 ± 0.52 | 28.52 ± 2.38 |
| Comparative Laminate Side B | 6.45 ± 0.43 | 25.72 ± 2.68 |
| Inventive Laminate 1 Side A | 4.67 ± 0.28 | 8.28 ± 0.64 |
| Inventive Laminate 1 Side B | 4.48 ± 0.54 | 8.28 ± 0.64 |
| Inventive Laminate 2 Side A | 5.58 ± 0.14 | 7.62 ± 0.45 |
| Inventive Laminate 2 Side B | 5.96 ± 0.24 | 7.01 ± 1.11 |

The laminates were evaluated for tensile performance in the ear shape described above. When using an ear during application of an absorbent article, an average strength (load at break) higher than 25 N and extension (at load at break) greater than 40 mm is preferred. The high strength ensures that the ear laminates will not break during application. The high extension at break signals to consumers that the absorbent article has sufficient stretch to provide desired fit. A shown in Table 7 and FIG. 8, the Comparative Laminate Example A delivered desired average load at break of 32.7 N for absorbent article application and average extension at break greater than 60 mm. However, the use of softer nonwovens in Inventive Laminates either improved the strength and/or improved the extension at break. The Inventive Laminate 1 with preferred softness delivered excellent Average Load at Break of about 36.4 N and Average Extension at Load at Break greater than 70 mm. Inventive Laminate Example 2 exhibited an Average Load at Break of about 26.4 N, while providing extremely high extension at break of about 80 mm. Importantly, all laminate examples were made under identical conditions.

TABLE 7

Laminate Tensile Data

| Example | Average Load at Break | Average Extension at Load at Break |
| --- | --- | --- |
| Comparative Laminate | 32.73 ± 3.39 N | 63.16 ± 3.13 mm |
| Laminate Example 1 (SB2') | 36.36 ± 3.59 N | 70.80 ± 2.51 mm |
| Laminate Example 2 (CD Rod) | 26.41 ± 1.84 N | 79.54 ± 2.26 mm |

Absorbent Article

Absorbent articles of the present invention may utilize the noncrimped spunbond fiber nonwoven webs described herein in any suitable location. In certain embodiments, a nonwoven web comprising one or more noncrimped spunbond fiber layers is present in an ear 30, waistband or side panel of a disposable article.

Figure 9:
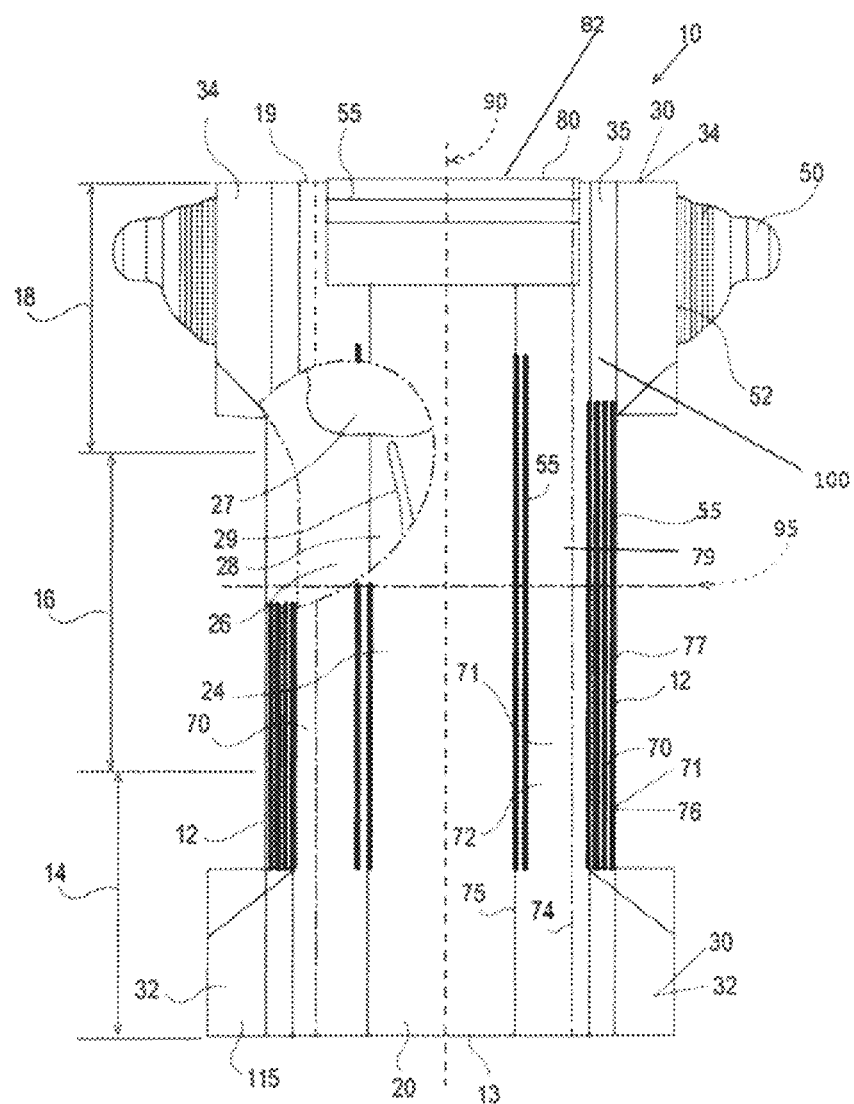
FIG. 9 is schematic, plan view of an exemplary absorbent article according to a nonlimiting embodiment of the present invention. The absorbent article is shown in a flat, uncontracted state.

FIG. 9 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 90 and a lateral centerline 95.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In one nonlimiting example, two channels are symmetrically disposed about the longitudinal axis.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet:

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 10 may include one or more ears 30, including for example front ears disposed in the first waist region and/or back ears disposed in the second waist region. The ears 30 may be integral with the chassis or discrete elements joined to the chassis 20 at a chassis attachment bond 35, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

As illustrated in FIG. 6, ears may include a distal edge 36 and a proximate edge 38. The distal edge 36 is the free distal longitudinal edge of the ear. The proximate edge 38 is substantially opposed to the distal edge 36. The proximate edge 38 is joined to or overlapped with the chassis when the ear is joined to the chassis, or is the side defined by a line extending from longitudinal side 12 in the widest area of the crotch region and running parallel to the longitudinal centerline in the case of integral ears. Ears may further include a first lateral edge 40 and an opposing second lateral edge 42. An ear may additional comprise a maximum width, W, extending between the distal edge and proximate edge and a length extending between the first and second lateral edges. In some instances, the length may vary at portions along the width of the ear, as shown in FIG. 6. For instance, the ear may comprise a maximum length along its proximate edge 38 and slope or otherwise vary such that the ear comprises a minimum length on its distal edge 36. In some embodiments, the ear 30 may include elastomers, such that the ear is stretchable.

In certain embodiments, the ears 30 may be formed of a stretch laminate, having elastomeric layer(s), which also results in the ear being stretchable. The ear 30 may be laterally-extensible. In some embodiments, the ear is elastic when stretched in the lateral direction. In further embodiments, the ear 30 may extend more in the lateral direction than in the longitudinal direction. Alternatively, the ear may extend more in the longitudinal direction than in the lateral direction.

In some embodiments, the ear comprises the laminate 310 having any of the features discussed above.

The absorbent article 10 may also include a fastening system 50. When fastened, the fastening system 50 interconnects the first waist region 16 and the rear waist region 18 resulting in a waist circumference that may encircle the wearer during wear of the absorbent article 10. The fastening system 50 may comprise a fastening elements such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 50 and/or the element is foldable.

The fastening system 50 may be joined to any suitable portion of the article 10 by any suitable means. In some embodiments, the fastening system is joined to the ear 30 at a fastener attachment bond 52. The fastening system may be joined to the ear between layers, or joined to the ear on an exterior surface of the ear, or joined to a body-facing surface of the ear or a garment facing surface. In one nonlimiting example, the fastening system 50 and/or fastening elements are ultrasonically bonded to the ear 30. The fastening attachment bond 52 comprises a maximum length, measured parallel to the longitudinal centerline. The maximum length may be about 30 mm or less, or about 28 mm or less, or from about 20 mm to about 35 mm, reciting for said range every 1 mm increment therein. The fastening attachment bond may join the fastening system to one or more layers of the ear.

The fastening system 50 may be joined to ear at the distal side 36. The nonwoven layer(s) 300, 304 may be folded at the fastening attachment bond and/or at the distal side. The fastening system may be disposed in the second inelastic region 312. In further embodiments, the fastening system 50 is joined in the elastic region 306 of the ear. Joining the fastening system to the ear in the elastic region 306 improves the overall strength of the ear/fastening system combination during use and/or application.

Leg Gasketing System

Returning to FIG. 9, the absorbent article 10 may comprise a leg gasketing system 70 attached to the chassis 20, which may comprise one or more cuffs 71. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximate edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 90 and are at least present in the crotch region. The barrier leg cuffs may be joined at the proximate edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximate edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, Ser. No. 14/077,708; U.S. Pat. Nos. 8,939,957; 3,860, 003; 7,435,243; 8,062,279.

Elastic Waist Feature

The absorbent article 10 may comprise at least one elastic waist feature 80 that helps to provide improved fit and containment, as shown in FIG. 9. The elastic waist feature 80 is generally intended to expand and contract to dynamically fit the wearer's waist. Elasticized waist features include waistbands, waist cuffs having pockets formed from a portion of the waist feature 80 that is unattached from the chassis 20, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 20 in the first waist region 14 and/or in the second waist region 16. The waist feature can be used in conjunction with the ear 30 to provide desirable stretch and flexibility for proper fit of the article on the wearer.

Packages

Absorbent articles comprising the noncrimped spunbond fiber nonwoven web or laminate of the present invention may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 10:
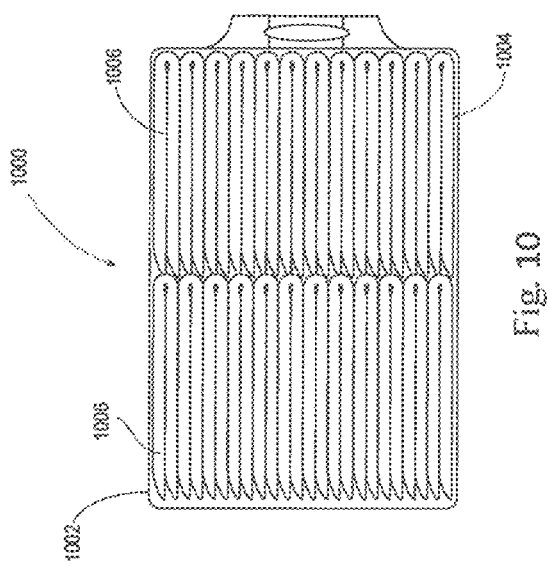
FIG. 10 is a schematic perspective view of a package in accordance with one embodiment of the present invention.

FIG. 10 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Combinations

A. An absorbent article comprising:
   a first waist region, a second waist region, a crotch region disposed between the first and second waist regions;
   a chassis comprising a topsheet, a backsheet, and an absorbent core disposed between the topsheet and backsheet; and
   an ear joined to the chassis and comprising:
   a laminate comprising a first nonwoven and second nonwoven and an elastomeric material sandwiched between said first and second nonwovens, wherein the laminate further comprises a plurality of ultrasonic bonds; and
   wherein the first nonwoven comprises an exterior surface having an average TS750 value of 5 db V2rms or less.

B. The absorbent article of paragraph A wherein the laminate comprises a first inelastic region and an elastic region, wherein the first inelastic region is void of the elastomeric material and wherein the exterior surface of the first nonwoven in the elastic region comprises an average TS7 value of 12 db V2rms or less.

C. The absorbent article of paragraphs A or B wherein the laminate comprises a first inelastic region and an elastic region, wherein the first inelastic region is void of the elastomeric material and wherein the exterior surface of the first nonwoven in the elastic region comprises an average TS750 value of 100 db V2rms or less.

D. The absorbent article of any of the preceding paragraphs wherein the laminate comprises a first inelastic region and an elastic region, wherein the first inelastic region is void of the elastomeric material and wherein the exterior surface of the first nonwoven in the first inelastic region comprises an average TS750 value of 10 db V2rms or less.

E. The absorbent article of any of the preceding paragraphs wherein the laminate comprises an Average Load at Break of 25N or greater.

F. The absorbent article of preceding paragraphs wherein the first nonwoven and/or the second nonwoven comprises a spunbond noncrimped fiber nonwoven.

G. The absorbent article of any of the preceding paragraphs wherein the first nonwoven and/or the second nonwoven comprises an Average Normalized Peak Force of at least 0.160 (N/cm)/(g/m2).

H. The absorbent article of any of the preceding paragraphs wherein the first nonwoven and/or the second nonwoven comprises an Average % Lateral Strain at Peak Force of 60% or less.

I. The absorbent article of paragraph H wherein the Average % Lateral Strain at Peak Force of 40% or more.

J. The absorbent article of any of the preceding paragraphs wherein the first nonwoven and/or second nonwoven has an Average Bond Area of about 12% or less.

K. The absorbent article any of the preceding paragraphs wherein the first nonwoven and/or second nonwoven comprises an average bond major dimension of at least 1.25 mm.

L. The absorbent article of any of the preceding paragraphs wherein the first nonwoven and/or second nonwoven comprises a Bond Site Area of 0.5 mm$^2$ or greater.

M. The absorbent article of any of the preceding paragraphs the second nonwoven comprises a second exterior surface having an average TS750 value of 5 db V2rms or less.

N. The absorbent article of any of the preceding paragraphs wherein the first nonwoven is void of crimped fibers.

O. The absorbent article of claim 14 wherein the first nonwoven comprises An Average Bond Width of 1.25 mm or greater.

P. The absorbent article of claim 16 wherein the first nonwoven comprises an Average Bond Height of 1.25 mm or greater.

Q. The absorbent article of claim 14 wherein the first nonwoven comprises an Average TS750 value of 5 db V2rms or less.

Test Methods
Bond Dimensions Test Method

Nonwoven Bond Shape Measurements are performed on reflected light microscopy images generated using a stereo light microscope (such as Zeiss V20 Stereoscope) and attached camera (such as the Carl Zeiss AxioCam MRcS). Measurements are performed using Image Pro Plus software (Version 7.0.0.591, Media Cybernetics, USA) calibrated against a ruler that was placed within the image when it was acquired.

Sample Preparation and Testing Procedure

For nonwovens, test samples are prepared by cutting square samples of approximately 6.5 cm (longitudinal)×3.5 cm (lateral) samples from the nonwoven web. For laminates, sample can be collected from the area where there is no corrugation and nonwoven surface is flat, such as inelastic area in the stretch ear construction disclosed above. Care should be taken to distinguish nonwoven thermal bond pattern from the ultrasonic bond pattern or other form of layer lamination pattern (e.g., adhesive pattern). If the larger sample is not available, a smaller sample with one repeat nonwoven bond pattern can be used. These samples are Au coated (~700 angstrom film deposition) in a sputter coater (such as Denton Desk V) to give bond sites greater contrast. Images are acquired with a horizontal field width of 27.3 mm and vertical field width of 19.4 mm. A ruler is placed in each image parallel to the MD direction. All measurements except for the Bond Site Area and Bond Area Percentage are measured with the line tool in Image Pro Plus software; Bond Site Area and Bond Area Percentage are measured with the irregular area tool in Image Pro Plus software. FIGS. 2-4 illustrate the dimensions below, which are all are measured to accuracy of 0.01 mm:

Bond Width (N1)—the distance between the lateral extremities of a single bond as measured in the lateral direction;

Bond Height (N2)—the distance between the longitudinal extremities of a single bond as measured in the longitudinal direction;

Bond Thickness (N3)—maximum lateral thickness of a single bond;

Minimum Lateral Bond Distance (N4)—the minimum lateral distance between the lateral edges of two laterally adjacent, nonoverlapping bonds Minimum Longitudinal Bond Distance (N5)—the minimum longitudinal distance between the longitudinal edges of two longitudinally adjacent, nonoverlapping bonds in the longitudinal direction Minimum Lateral Row Offset (N6)—the smallest lateral distance between two laterally adjacent rows, as measured between the edges of said rows Minimum Longitudinal Column Offset (N7)—the smallest longitudinal distance between two longitudinally adjacent columns, as measured between the edges of said columns Bond Site Area (N8), which is the two dimensional area of a single bond.

Distances (N4, N5, N6, and N7) are measured between closest edges of the respective bonds.

Bond Area Percentage: Identify a single repeat pattern of bond shapes and areas between them, and enlarge the image such that an area larger than at least one repeat pattern fills the field of view. In Image Pro Plus, draw a rectangle that circumscribes the repeat pattern. Calculate area of the rectangle and record to the nearest 0.01 mm$^2$. Next, with the area tool, trace individual bond sites/shapes. Calculate Bond Area Percentage as follows:

$$\text{Bond Area \%} = \frac{\text{sum of bond site areas within repeat pattern}}{\text{total area of repeat pattern}} \times 100$$

A total of three measurements are made from one image, and arithmetic average of three measurements is reported for each parameter: Average Bond Area %, Average Bond Width ($N1_{av}$), Average Bond Height ($N2_{av}$), Average Bond Thickness ($N3_{av}$), Average Maximum Lateral Bond Distance ($N4_{av}$), Average Maximum Longitudinal Bond Distance ($N5_{av}$), Average Minimum Lateral Row Offset ($N6_{av}$), Average Minimum Longitudinal Column Offset ($N7_{av}$), and Average Bond Site Area ($N8_{av}$). If the sample is not large enough or three good measurements cannot be made for each parameter from one sample, three different samples, each with preferably one repeat bond pattern, should be used. If sample wider than one repeat bond pattern is not available, one should use multiple samples to identify repeat bond pattern and make the measurements as per the method above.

Tensile Test Method

Figure 12:
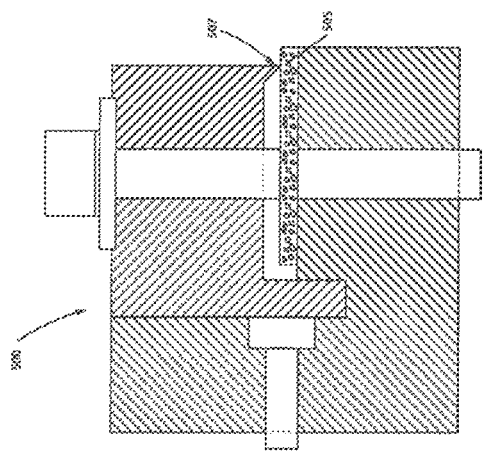
FIG. 12 is a schematic side elevation view of a grip suitable for use in the Tensile Test Method herein.
Figure 11:
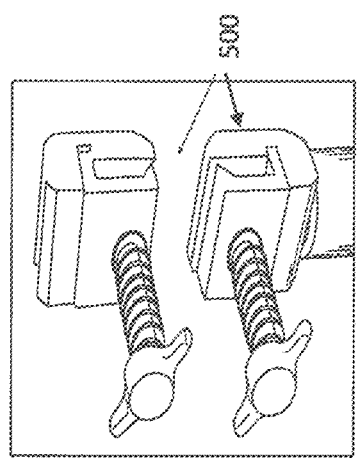
FIG. 11 is a schematic perspective view of grips suitable for use in the Tensile Test Method herein.

The Tensile Test is used to measure the strength of a specimen at a relatively high strain rate that represents product application. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Grips shown in the FIGS. 11 and 12 should be used to secure the specimens during tensile testing. (FIG. 12 is a side view of one of the grips in FIG. 11 with a material 507 to prevent slippage.) The opposing grips 500 may have the same width or different widths as specified.

(a) Grips

The line grips 500 are selected to provide a well-defined gauge and avoid undue slippage. The specimen is positioned such that it has minimal slack between the grips. The apexes 507 of the grips 500 are ground to give good gauge definition while avoiding damage or cutting of the specimen. The apexes are ground to provide a radius in the range of 0.5-1.0 mm. A portion of one or both grips 500 may be configured to include a material 505 that reduces the tendency of a specimen to slip, (e.g., a piece of urethane or neoprene rubber having a Shore A hardness of between 50 and 70) as shown in FIG. 12. Six inches wide top and bottom grips are used to clamp the specimen unless specified otherwise.

(b) Tensile Test of Specimen of Laminate or Ear

Ear laminates are generally bonded to chassis via thermal or adhesive or similar bonding. An ear should be separated from the chassis in a way that it is not damaged and performance of the ear is not altered. If the chassis bond is too strong, then the portion of the chassis joined to the ear should be cut within the chassis material but without damaging the ear. Folded fastening systems (e.g., release tapes covering fastening elements) should be unfolded.

The specimen is clamped in the top grip at a first grip location G1 which is inboard edge 52a of the fastener attachment bond 52 (see FIG. 6A). The grip line G1 is kept parallel to the longitudinal centerline of the product. If the fastener attachment bond is angled, the specimen is gripped at the center of the bond region and grip line is kept parallel to the longitudinal centerline of the product at the center. The width of the top grip should be equal to the maximum length of the fastener attachment bond 52 (L1) measured parallel to the longitudinal centerline of the article. If, at the G1 position, the length of the specimen is the same as the maximum length of the fastener attachment bond, then any grip width greater than the specimen length at G1 can be used. The specimen is mounted and hung from the top grip. The opposing edge 38 of the specimen is mounted in the bottom grip in relaxed condition. The bottom grip location G2 is adjusted so the specimen is gripped at the outboard edge 35b of the chassis bond. If the chassis bond is curvilinear, the specimen is gripped at the outboard edge of the outermost bond. The bottom grip is greater than the length of the ear at the second grip location, G2. The top and bottom grips are parallel to each other.

The specimen is tested as follows: The vertical distance (perpendicular to the grip line) from the first grip location, G1, to second grip location, G2, is measured to 0.1 mm using ruler and is used as gage length for the test. The specimen is tested at a test speed that provides 9.1 sec$^{-1}$ strain rate with the gage length selected for the specimen. Test speed in mm/second is calculated by multiplying 9.1 sec$^{-1}$ by the gage length in mm. Before testing, 5 mm of slack is put between the grips.

For standalone laminates, a sample is cut as per the dimensions outlined in Table 3, except as set forth in this paragraph. The Y width of the film is kept as provided in the laminate. If film width Y is smaller than W, than X and Z distances are maintained as outlined in Table 3. If X and Z dimensions cannot be maintained, then the specimen is cut in the shape set forth in Table 3 with film centered. Grip line G1 is still maintained at distance X when testing the specimen. Dimension Z is decided based on X and Y dimensions. If film width Y is the same as W, then G1 is maintained at X distance as outline in Table 3. The laminate is tested as described above with 55 mm gage length, and at 500 mm/sec test speed.

Each specimen is pulled to break. During testing, one of the grips is kept stationary and the opposing grip is moved. The force and actuator displacement data generated during the test are recorded using a MOOG SmarTEST ONE ST003014-205 standalone controller, with the data acquisition frequency set at 10 kHz. The maximum value of the resulting load data may be expressed as load at break in Newton. A total of five (5) specimens are run for example. The Average Load at Break, Average Extension at Load at break, and standard deviation of at least 4 specimens are recorded. If, standard deviation recorded is higher than 15%, a new set of five specimens is run.

(c) Tensile Test of Specimen from Nonwoven Web

A specimen measuring 16.8 mm (along the lateral direction of the web) by 127 mm (along the longitudinal direction of the web) of a given nonwoven web is delicately cut from the web. For purposes of equations below, the specimen length is 16.8 mm and the specimen width is 127 mm. The specimen is tested as follows: The gauge length (i.e. clamp to clamp separation) of the vertical distance from the first grip location, to the second grip location is 10 mm, and is measured to 0.1 mm accuracy using a ruler. The specimen is tested at a test speed that provides a cross-head displacement speed of approximately 6 m/s. Before testing, 5 mm of slack is put between the grips. The specimen is placed between the grips 500 such that the lateral direction of the specimen will be extended during the testing.

Each specimen is pulled until it ruptures (i.e. the post peak force response reaches a value less than 10% of the peak force). During testing, one of the grips is kept stationary and the opposing grip is moved. The force and actuator displacement data generated during the test are recorded using a MOOG SmarTEST ONE STO03014-205 standalone controller, with the data acquisition frequency set at 10 kHz. A total of five (5) specimens are run for example. Raw data for length (extension), and load (force) from the tensile tester are smoothed using 5 point simple moving average using formula below. The first moving average data point is arithmetic average of raw data points 1 to 5, and the second data point is the arithmetic average of the raw data points from 2 to 6. The moving average data table is used for the subsequent calculations.

$$\text{Moving Average Data Point 1} = \frac{\text{Raw Data 1} + \text{Raw Data 2} + \text{Raw Data 3} + \text{Raw Data 4} + \text{Raw Data 5}}{5}$$

In order to minimize the influence of the basis weight of each web sample being tested, each sample curve (moving average data curve) is normalized for the basis weight of the sample being tested (i.e. the values of the force applied are divided by the value of the basis weight of the web sample being tested), using the following formula:

$$\text{Normalized Force } \frac{\frac{N}{cm}}{\frac{g}{m^2}} = \frac{\left(\frac{\text{Force, } N}{\text{specimen width, cm}}\right)}{\left(\frac{\text{specimen mass, grams}}{(\text{specimen width, m}) \times (\text{specimen length, m})}\right)}$$

The strain of each sample is reported on the x axis in % Strain while the force applied to each sample (from moving average table) is reported on the y axis in Normalized Force $(N/cm)/(g/m^2)$. The % strain is calculated from the length between grip lines L, and initial gauge length, $L_0$, using the following formula:

$$\% \text{ Strain} = \frac{(L - L_0)}{L_0} \times 100$$

The Average Normalized Peak Force in $(N/cm)/(g/m^2)$, Average % Strain at Peak, and standard deviation of at least 3 specimens are recorded. If, standard deviation recorded is higher than 20%, a new set of four specimens is run. Peak is defined as the maximum force value followed by substantial drop in force. Break is defined as the point where the material fractures or ruptures, and force drops rapidly to zero value. % Strain at Peak is defined as the % Strain at the maximum force.

Basis Weight Test Method

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{(\text{Weight of the specimen in grams})}{(\text{Length of the specimen in meter})}$$
$$(\text{Width of the specimen in meter})$$

For calculating the basis weight of a substrate, a total 3 rectilinear specimens at least 10 mm×25 mm are used.

The average basis weight and standard deviation are recorded.

Nonwoven specimens from ears are obtained as follows. The specimen should be taken from a region having no additional material (i.e., only nonwoven). Each nonwoven layer is separated from the other layers of the ear without damaging or tearing the nonwoven layer. If one continuous nonwoven covers outboard and inboard inelastic regions of the ear, said nonwoven is separated from the inelastic regions and used as the specimen. If the nonwoven layer is inseparable from other ear layers, the specimen is collected from the outboard inelastic region of the ear. If the outboard inelastic region is smaller than the prescribed specimen dimensions or has additional material (other than nonwoven layers), and if the inboard inelastic region has identical nonwovens as the outboard inelastic region, then the specimen (either nonwoven layer or the combination of nonwoven layers) is collected from the inboard inelastic region. If the nonwoven layers in the inelastic region are identical and/or inseparable, then the calculated basis weight of the specimen is divided by the number of nonwoven layers to get the individual nonwoven basis weight.

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut in dimension of 10 mm in the intended stretch direction of the laminate by 25.4 mm in the direction perpendicular to the intended stretch direction of the laminate. A specimen is collected from an inelastic region or an elastic region of the laminate (i.e., the sample does not cross into both inelastic and elastic regions).

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force. This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, Hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.
  ii. Length of specimen between the grips on first cycle at the 100% strain ($l_{max}$) to the nearest 0.001 mm.
  iii. Length of specimen between the grips at a second cycle load force of 7 gram-force ($l_{ext}$) to the nearest 0.001 mm.
  iv. % Set, which is defined as $(l_{ext}-l_{ini})/(l_{max}-l_{ini})*100\%$ to the nearest 0.01%.

The testing is repeated for six separate samples and the average and standard deviation reported.

Softness Test Method

TS7 and TS750 values are measured using an EMTEC Tissue Softness Analyzer ("Emtec TSA") (Emtec Electronic GmbH, Leipzig, Germany) interfaced with a computer running Emtec TSA software (version 3.19 or equivalent). According to Emtec, the TS7 value correlates with the real material softness, while the TS750 value correlates with the felt smoothness/roughness of the material. The Emtec TSA comprises a rotor with vertical blades which rotate on the test sample at a defined and calibrated rotational speed (set by manufacturer) and contact force of 100 mN. Contact between the vertical blades and the test piece creates vibrations, which create sound that is recorded by a microphone within the instrument. The recorded sound file is then analyzed by the Emtec TSA software.

Sample Preparation

Test samples are prepared by cutting square or circular samples from a finished product. Test samples are cut to a length and width (or diameter if circular) of about 90 mm, and no greater than 120 mm, in dimension. If the finished product has a discrete section of elastic region (i.e. elastic region is shorter in one or more dimensions than nonwoven facing-layers), a set of rectilinear specimens 76 mm±3 mm long in the primary stretch direction, and 100 mm±3 mm wide in the perpendicular direction is cut from the product part, with the elastic region centered in the rectilinear specimen. Test samples are selected to avoid creases or folds within the testing region. Prepare 8 substantially similar replicate samples for testing. Equilibrate all samples at TAPPI standard temperature and relative humidity conditions (23° C.±2 C. ° and 50%±2%) for at least 1 hour prior to conducting the TSA testing, which is also conducted under TAPPI conditions.

Testing Procedure

Calibrate the instrument according to the manufacturer's instructions using the 1-point calibration method with Emtec reference standards ("ref.2 samples"). If these reference samples are no longer available, use the appropriate reference samples provided by the manufacturer. Calibrate the instrument according to the manufacturer's recommendation and instruction, so that the results will be comparable to those obtained when using the 1-point calibration method with Emtec reference standards ("ref.2 samples").

Mount the test sample into the instrument and ensure the sample is clamped into the TSA instrument properly with its first surface facing upwards. For samples with a discrete section of elastic region, ensure that the elastic region is centered below the Emtec vertical blades, and then perform the test according to the manufacturer's instructions. When complete, the software displays values for TS7 and TS750. Record each of these values to the nearest 0.01 dB $V^2$ rms. The test piece is then removed from the instrument and discarded. This testing is performed individually on the first surface of four of the replicate samples, and on the second surface of the other four replicate samples.

The four test result values for TS7 and TS750 from the first surface are averaged (using a simple numerical average); the same is done for the four test result values for TS7 and TS750 from the second surface. Report the individual average values of TS7 and TS750 for both the first and second surfaces on a particular test sample to the nearest 0.01 dB $V^2$ rms.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a first waist region, a second waist region, a crotch region disposed between the first and second waist regions;
   a chassis comprising a topsheet, a backsheet, and an absorbent core disposed between the topsheet and backsheet; and
   an ear joined to the chassis and comprising:
     a laminate comprising a first nonwoven and second nonwoven and an elastomeric material sandwiched between said first and second nonwovens, wherein the laminate further comprises a plurality of ultrasonic bonds;
     wherein the first nonwoven comprises an exterior surface having an average TS750 value of 5 db $V^2$rms or less; and
     wherein the laminate comprises a first inelastic region and an elastic region, wherein the first inelastic region is void of elastomeric material and wherein the exterior surface of the first nonwoven in the elastic region comprises an average TS7 value of 12 db $V^2$rms or less.

2. The absorbent article of claim 1 wherein the exterior surface of the first nonwoven in the elastic region comprises an average TS750 value of 100 db $V^2$rms or less.

3. The absorbent article of claim 1 wherein the exterior surface of the first nonwoven in the first inelastic region comprises an average TS750 value of 10 db $V^2$rms or less.

4. The absorbent article of claim 1 wherein the laminate comprises an Average Load at Break of 25N or greater.

5. The absorbent article of claim 1 wherein the first nonwoven comprises a spunbond noncrimped fiber nonwoven.

6. The absorbent article of claim 5 wherein the first nonwoven comprises an Average Normalized Peak Force of at least 0.160 (N/cm)/(g/m$^2$).

7. The absorbent article of claim 5 wherein the first nonwoven comprises an Average % Strain at Peak Force of 60% or less.

8. The absorbent article of claim 7 wherein the Average % Strain at Peak Force of 40% or more.

9. The absorbent article of claim 1 wherein the first nonwoven has an average bond area of about 12% or less.

10. The absorbent article of claim 1 wherein the first nonwoven comprises an average bond major dimension of at least 1.25 mm.

11. The absorbent article of claim 10 wherein the first nonwoven comprises a bond site area of 0.5 mm$^2$ or greater.

12. The absorbent article of claim 1 wherein the second nonwoven comprises a second exterior surface having an average TS750 value of 5 db $V^2$rms or less.

13. An absorbent article comprising:
a first waist region, a second waist region, a crotch region disposed between the first and second waist regions;
a chassis comprising a topsheet, a backsheet, and an absorbent core disposed between the topsheet and backsheet; and
an ear joined to the chassis and comprising:
a laminate comprising a first spunbond nonwoven and an elastomeric material, wherein the laminate further comprises a plurality of ultrasonic bonds, an inelastic region void of the elastomeric material and an elastic region;
the first spunbond nonwoven has an Average Bond Area of 12% or less and an Average Normalized Peak Force of at least 0.160 (N/cm)/(g/m$^2$); and
wherein the first spunbond nonwoven comprises an exterior surface having an average TS750 value of 10 db V2rms or less in the inelastic region.

14. The absorbent article of claim 13 wherein the first spunbond nonwoven is void of crimped fibers.

15. The absorbent article of claim 13 wherein the first spunbond nonwoven comprises an average bond width of 1.25 mm or greater.

16. The absorbent article of claim 15 wherein the first spunbond nonwoven comprises an average bond height of 1.25 mm or greater.

17. The absorbent article of claim 13 wherein the first spunbond nonwoven comprises an average TS750 value of 5 db $V^2$rms or less.

18. An absorbent article comprising:
a first waist region, a second waist region, a crotch region disposed between the first and second waist regions;
a chassis comprising a topsheet, a backsheet, and an absorbent core disposed between the topsheet and backsheet; and
an ear joined to the chassis and comprising:
a laminate comprising a first spunbond nonwoven and an elastomeric material, wherein the laminate further comprises a plurality of ultrasonic bonds, an elastic region, and an inelastic region void of the elastomeric material; and
the first spunbond nonwoven has an Average Bond Area of 12% or less and an average bond major dimension of 1.25 mm or greater; and
wherein an exterior surface of the first spunbond nonwoven in the elastic region comprises an average TS750 value of 100 db $V^2$rms or less.

* * * * *